United States Patent
Kis, Jr. et al.

(10) Patent No.: US 9,140,637 B2
(45) Date of Patent: Sep. 22, 2015

(54) METHOD AND APPARATUS FOR SIMULATING HEAD IMPACTS FOR HELMET TESTING

(76) Inventors: Mihaly Kis, Jr., Oakville (CA); Mihaly Kis, Sr., Stoney Creek (CA); Fraser Worden Saunders, Kingston (CA); Martin William ten Hove, Kingston (CA)

(*) Notice: Subject to any disclaimer, the term of this patent is extended or adjusted under 35 U.S.C. 154(b) by 599 days.

(21) Appl. No.: 13/077,366

(22) Filed: Mar. 31, 2011

(65) Prior Publication Data

US 2012/0247178 A1    Oct. 4, 2012

(51) Int. Cl.
| | | |
|---|---|---|
| *G01M 7/00* | (2006.01) | |
| *G01N 3/30* | (2006.01) | |
| G01M 17/007 | (2006.01) | |
| A42B 3/04 | (2006.01) | |
| G01N 33/00 | (2006.01) | |

(52) U.S. Cl.
CPC ............ *G01N 3/30* (2013.01); *A42B 3/0433* (2013.01); *G01M 17/0078* (2013.01); *G01N 2033/008* (2013.01); *G01N 2033/0086* (2013.01)

(58) Field of Classification Search
CPC ..... G01M 17/0078; G01M 7/08; G01M 7/00; G01N 3/30
USPC ...................................... 73/12.04
See application file for complete search history.

(56) References Cited

U.S. PATENT DOCUMENTS

| | | | |
|---|---|---|---|
| 3,331,236 A * | 7/1967 | Payne et al. .......... | 73/12.04 |
| 3,559,492 A | 2/1971 | Erdley | |
| 3,707,722 A | 12/1972 | Itoh | |
| 4,161,874 A | 7/1979 | Specker et al. | |
| 4,299,576 A | 11/1981 | Kron | |
| 5,325,701 A | 7/1994 | Zilliacus | |
| 5,487,305 A | 1/1996 | Ristic et al. | |

(Continued)

FOREIGN PATENT DOCUMENTS

| | | |
|---|---|---|
| EP | 0 235 534 A1 | 9/1987 |
| EP | 0 351 430 A1 | 1/1990 |

(Continued)

OTHER PUBLICATIONS

M. Kis, F. Saunders, M.W. Ten Hove and J.R. Leslie, Rotational Acceleration Measurements—Evaluating Helmet Protection, The Canadian Journal of Neurological Sciences, Nov. 2004, pp. 499-503, vol. 31, No. 4.

(Continued)

*Primary Examiner* — Lisa Caputo
*Assistant Examiner* — Octavia Hollington

(57) ABSTRACT

An apparatus is disclosed that includes a frame, an impact delivery unit for delivering an impact force and at least one head form. The head form is adapted to be mounted to the frame such that the impact delivery unit can deliver an impact force to a designated location on the head form. The head form is configured to have a helmet installed thereon. The head form is selectively rotatable about each of a plurality of different axes of rotation, wherein movement of the head form is constrained to be able to move only in rotation and in rotation about only one axis of rotation of the plurality of axes at any time. A measuring system provides an indicator of the rotational acceleration of the head form when rotated about each of the plurality of axes. Also disclosed are methods for comparing the degree of protection afforded by first and second helmets.

36 Claims, 31 Drawing Sheets

(56) References Cited

U.S. PATENT DOCUMENTS

| | | | |
|---|---|---|---|
| 5,539,935 | A | 7/1996 | Rush, III |
| 5,621,922 | A * | 4/1997 | Rush, III .................... 2/422 |
| 5,978,972 | A | 11/1999 | Stewart et al. |
| 6,361,507 | B1 | 3/2002 | Foxlin |
| 6,786,877 | B2 | 9/2004 | Foxlin |
| 6,826,509 | B2 | 11/2004 | Crisco, III et al. |
| 6,871,525 | B2 * | 3/2005 | Withnall et al. ............ 73/12.14 |
| 6,941,952 | B1 | 9/2005 | Rush, III |
| 7,076,811 | B2 | 7/2006 | Puchalski |
| 7,383,728 | B2 | 6/2008 | Noble et al. |
| 7,386,401 | B2 | 6/2008 | Vock et al. |
| 7,509,835 | B2 | 3/2009 | Beck |
| 7,526,389 | B2 | 4/2009 | Greenwald et al. |
| 7,634,379 | B2 | 12/2009 | Noble |
| 7,693,668 | B2 | 4/2010 | Vock et al. |
| 7,743,640 | B2 * | 6/2010 | Lampe et al. ................ 73/12.04 |
| 8,554,509 | B2 * | 10/2013 | Crisco et al. .................. 702/141 |
| 2004/0074283 | A1 | 4/2004 | Withnall et al. |
| 2005/0177929 | A1 | 8/2005 | Greenwald et al. |
| 2006/0038694 | A1 | 2/2006 | Naunheim et al. |
| 2008/0155735 | A1 | 7/2008 | Ferrara |
| 2008/0256685 | A1 | 10/2008 | Lampe et al. |
| 2010/0083424 | A1 | 4/2010 | Linares |
| 2010/0102970 | A1 | 4/2010 | Hertz |

FOREIGN PATENT DOCUMENTS

| | | |
|---|---|---|
| EP | 0 392 812 A2 | 10/1990 |
| EP | 0 850 575 A1 | 7/1998 |
| EP | 0 674 767 B1 | 8/1998 |
| WO | WO 03/068339 A1 | 8/2003 |
| WO | WO 2006/005143 A1 | 1/2006 |

OTHER PUBLICATIONS

David C. Viano, Dr. med., Ph.D., Ira R. Casson, M.D. And Elliot J. Pellman, M.D., Concussion in Professional Football: Biomechanics of the Struck Player—Part 14, Neurosurgery, Aug. 2007, pp. 313-328, vol. 61, No. 2.

H. Cairns, D.M., F.R.C.S. and H. Holbourn, D.Phil., Head Injuries in Motor-Cyclists with Special Reference to Crash Helmets, British Medical Journal, May 15, 1943, pp. 591-598.

J. Hume Adams, FRCPath, D. I. Graham, MRCPath, Lilian S. Murray, BSc and Grace Scott, MBChB, Diffuse Axonal Injury Due to Nonmissile Head Injury in Humans: An Analysis of 45 Cases, Annals of Neurology, Dec. 1982, pp. 557-563, vol. 12, No. 6.

Thomas A. Gennarelli, MD, Lawrence E. Thibault, ScD, J. Hume Adams, MB, PhD, FRCPath, David I. Graham, MB, PhD, MRCPath, Carson J. Thompson, MD, and Robert P. Marcincin, MD, Diffuse Axonal Injury and Traumatic Coma in the Primate, Annals of Neurology, Dec. 1982, pp. 564-574, vol. 12, No. 6.

W. J. Curnow, The Efficacy of Bicycle Helmets Against Brain Injury, Accident Analysis and Prevention 35, 2003, pp. 287-292.

Elliot J. Pellman, M.D., David C. Viano, Dr. med., Ph.D., Chris Withnall, B.S., Nick Shewchenko, B.S., Cynthia A. Bir, Ph.D. and P. David Halstead, Concussion in Professional Football: Helmet Testing to Assess Impact Performance—Part 11, Neurosurgery, Jan. 2006, pp. 78-96, vol. 58, No. 1.

AS McIntosh and D Janda, Evaluation of Cricket Helmet Performance and Comparison with Baseball and Ice Hockey Helmets, British Journal of Sports Medicine, 2003, pp. 325-330, vol. 37, Issue 4.

PDF Brochure for Biokinetics and Associates Ltd., "Linear Impactor (LI)" (1 page), http://www.biokinetics.com/images/stories/products/impactor/Linear_Impactor_Brochure_V02.pdf, File date: Aug. 9, 2010.

PDF Brochure for Biokinetics and Associates Ltd., "Helmet Impact Tower" (2 pages), http://www.biokinetics.com/images/stories/products/hit/HIT_-_Brochure_20100902.pdf, File date: Aug. 9, 2010.

Evan Warner and Nolan Davis, A Study of the Forces Caused by Rotational and Translational Accelarations Associated with Head Injuries, Reinbolt Research Group, The University of Tennessee, http://rrg.utk.edu/resources/BME473/lectures/presentation_team_24.pdf (undated).

* cited by examiner

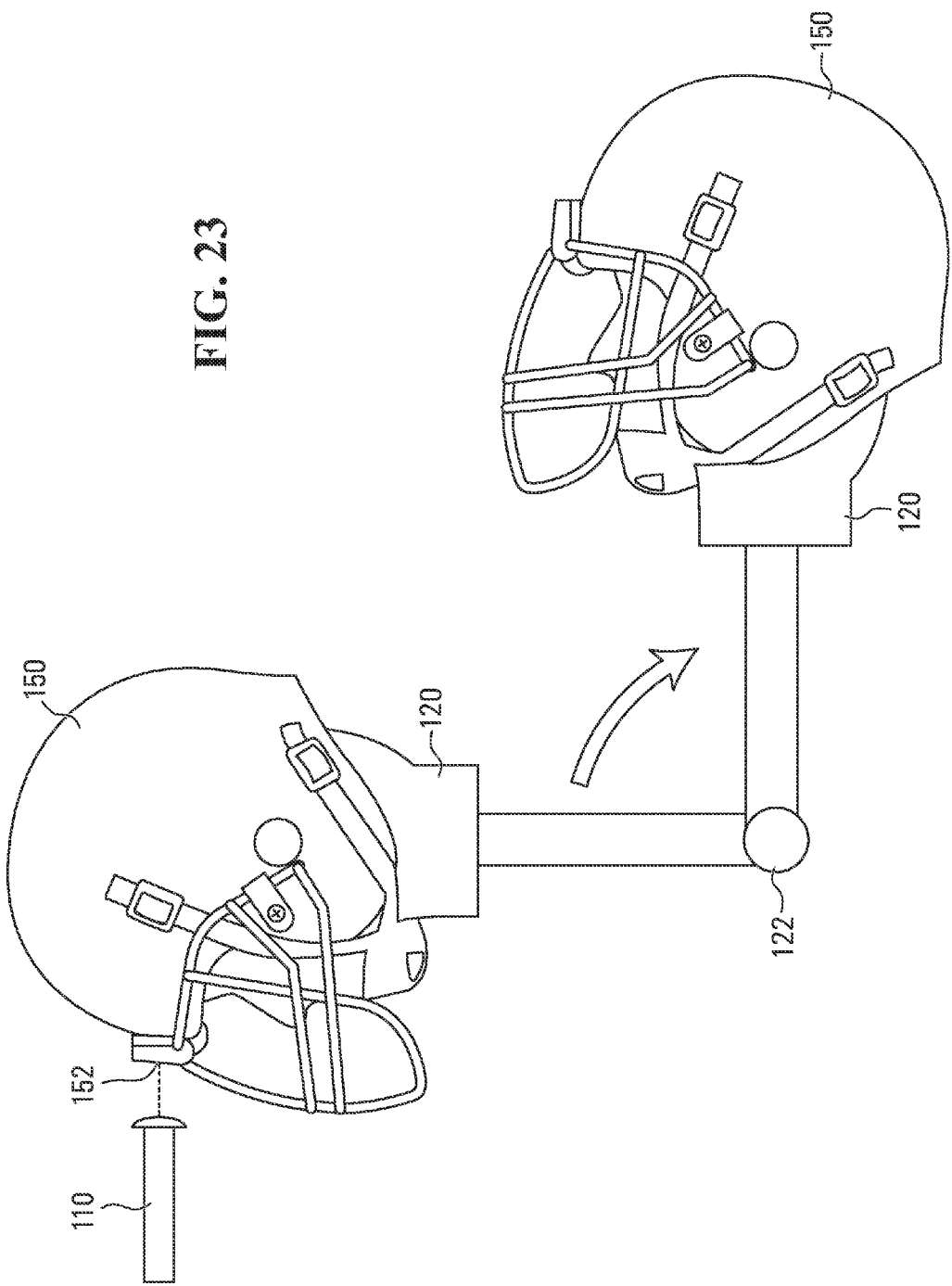

Helmeted Headform

Unhelmeted Headform

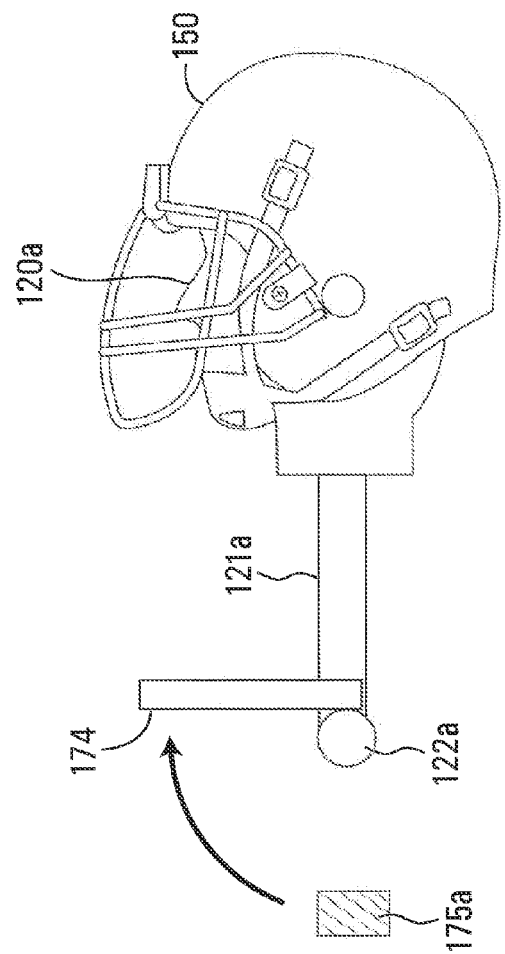
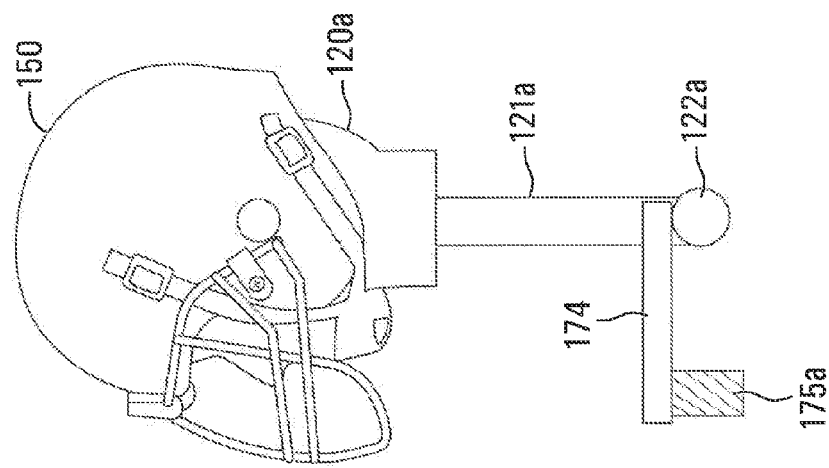
FIG. 30A
FIG. 30B

METHOD AND APPARATUS FOR SIMULATING HEAD IMPACTS FOR HELMET TESTING

FIELD OF THE INVENTION

The present invention relates to a method and apparatus for simulating head impacts for helmet testing.

BACKGROUND

Various activities, such as for example contact sports or military operations, require the use of helmets to attempt to protect participants from injury to their heads due to impact forces that may be sustained during such activities. As helmets protect against head injury, it follows that the science of head injury should underlie the development and testing of helmets to achieve the greatest effectiveness.

Concussion science is not well understood. Holborn, in 1943 and 1945, proposed rotational acceleration as the primary concussive mechanism. Gurdjian, Lissner, and others in the 1950's and 60's however thought that deformation of the skull and pressure waves that propogated through the cranial vault were the most offending agents. In the 1970's and 80's experiments by Gennarelli, Ommaya, Thibault, Adams and others produced head injuries in monkeys and concluded that rotational acceleration injuries produced diffuse, deep brain injury and that linear acceleration produced focal, superficial damage: concussive injury was more easily produced with rotational acceleration. Recent experiments by Hardy using high-speed bi-planar x-ray imaging to track the displacement of neutral-density radio-opaque markers in the brain of cadavers during impacts have shown that all head impacts produce a figure of eight movement within the brain involving both linear and rotational components. Bayly et al used human volunteers and MRI imaging to measure brain deformation and found that angular acceleration and rotation occurs with linear acceleration forces.

Helmet testing in sport became formalized with motor vehicle racing. The British Standards Institute produced documents in 1952 and 1954 pertaining to the testing of motor vehicle helmets. They dropped a wooden block onto a helmeted headform made of horizontally laminated birch, with a moisture of 12% and that the wood be straight, without defect or "dote" (Neuman). In 1956 the Sport Car Club of America asked George Snively to investigate helmet performance. He put helmets on cadavers and subjected them to severe impacts recording the presence or absence of a skull fracture. He improved his technique and in 1969 put helmets on a 12 lb. K-1A magnesium alloy head form and measured the acceleration to impact. In 1966 the American Standards Association published standards using Snively testing techniques of impacting a mobile metal head form but suggested that there should be time limits placed upon the impact. In 1969 the National Operating Committee for Athletic Equipment (NOCSAE) published a standard for football helmets incorporating a more lifelike head form and a drop test paradigm. The helmeted head form is dropped from a prescribed distance onto an anvil and the central accelerometer measures the deceleration. Maximum values of deceleration are used for certification. These values typically range from 275-300×g (force of gravity). This has been a standard method of helmet testing ever since.

It has been recognized for some time that helmet testing has not taken rotational acceleration into account and that helmets may protect against certain types of severe injury but may not be protecting against concussive injury. Science has found that a rotational force component is present in every impact but this is has not been properly accounted for in present helmet standards and certification. Biokinetics and Associates Ltd. is an engineering firm that was employed by the National Football league for helmet testing and developed a pendulum impact test onto a mobile helmeted head form. Pellman *Neurosurgery* 58:78-96, 2006 reported that data from this has been used to update the NOCSAE drop test by placing the impactor and helmeted mobile head form in a horizontal plane. Results from these recent attempts have been questioned as to their reproducibility and clinical relevance.

A need exists for an improved method and apparatus for testing helmets.

SUMMARY OF THE INVENTION

In accordance with an aspect of the present invention, there is provided an apparatus comprising: a frame; an impact delivery unit for delivering an impact force; at least one head form adapted to be mounted to the frame such that the impact delivery unit can deliver an impact force to a designated location on the at least one head form; the head form being configured to have a helmet installed thereon; the at least one head form being selectively rotatable about each of a plurality of different axes of rotation, wherein movement of the at least one head form is constrained to be able to move only in rotation and in rotation about only one axis of rotation of the plurality of axes at any time; a measuring system for providing an indicator of the rotational acceleration of the at least one head form when rotated about each of the plurality of axes; wherein, when the impact delivery unit delivers a plurality of impact forces to the designated location on the at least one head form, such that the at least one head form rotates separately about each axis of rotation of the plurality of axes, and wherein the measurement system provides indicators of rotational accelerations about each of the plurality of axes of rotation of the at least one head form during separate rotations about each axis of the plurality of axes of rotation.

In accordance with an aspect of the present invention, there is provided a method of testing a helmet, the method comprising: providing an impact delivery unit having a force actuator for delivering an impact force; providing at least one head form such that the impact delivery unit can deliver an impact force to the at least one head form; impacting the at least one head form with the force actuator so as to rotate the at least one head form about a plurality of different axes of rotation in sequence, wherein movement of the at least one head form during each rotation is constrained to be able to move only in rotation and only about one axis of rotation of the plurality of axes at any time; obtaining an indicator of each acceleration of the at least one head form when rotated about each of the plurality of axes; from the indicators of acceleration, determining the rotational acceleration of each the head form during rotations about each of the plurality of axes of rotation.

In accordance with an aspect of the present invention, there is provided a method for testing a helmet, the method comprising: selecting a first head form from a plurality of head forms, each of the plurality of head forms each being configured to rotate only about a different axis of rotation of a plurality of axes of rotation; installing a helmet on the first head form; exerting a force against the helmet at a designated location to thereby cause the selected head form to rotate about a first axis of rotation; measuring an indicator of rotational acceleration about the first axis of rotation of the selected head form; determining a rotational acceleration of the selected head form about the corresponding first axis of rotation; selecting a second head form from a plurality of head forms; installing the helmet on the second head form; exerting a force against the helmet at a designated location to thereby cause the selected head form to rotate about the second axis of rotation; measuring an indicator of rotational acceleration about the second axis of the selected head form; determining a rotational acceleration of the selected head form about the second axis of rotation.

In accordance with an aspect of the present invention, there is provided a method for testing a helmet, the method comprising: i. selecting a head form adapted and constrained to rotate about a first axis of rotation of a plurality of axes of rotation; ii. impacting the head form at a first designated location with a force actuator operable to exert a constant force against the head form to thereby cause the selected head form to rotate about the one axis of rotation; iii. measuring an indicator of rotational acceleration in relation to the first axis of the head form; iv. determining a baseline rotational acceleration in relation to the first axis of the head form; v. installing a helmet on the head form; vi. impacting the helmet installed on the head form at the first designated location with a force actuator operable to exert the constant force against the head form to thereby cause the selected head form to rotate about the one axis of rotation; vii. measuring an indicator of rotational acceleration in relation to the first axis of the head form; viii. determining a rotational acceleration of the selected head form when the helmet is installed on the head form; and ix. determining a degree of protection against rotational acceleration in relation to the first axis afforded by the helmet for the impact point; x. selecting a head form adapted and constrained to rotate about a second axis of rotation of a plurality of axes of rotation; xi. impacting the head form at a second designated location with a force actuator operable to exert a constant force against the head form to thereby cause the selected head form to rotate about the second axis of rotation; xii. measuring an indicator of rotational acceleration of the head form; xiii. determining a baseline rotational acceleration in relation to the second axis of the head form; xiv. installing the helmet on the head form; xv. impacting the helmet installed on the head form at the second designated location with a force actuator operable to exert the constant force against the head form to thereby cause the selected head form to rotate about the one axis of rotation; xvi. measuring an indictor of rotational acceleration in relation to the second axis of the head form; xvii. determining a rotational acceleration in relation to the second axis of the selected head form when the helmet is installed on the head form; and xviii. determining a degree of protection against rotational acceleration in relation to the second axis afforded by the helmet for the impact point.

In accordance with an aspect of the present invention, there is provided a method for testing a helmet, the method comprising: providing a head form adapted and constrained to rotate separately about a first axis of rotation and a second axis of rotation; generating a baseline rotational acceleration in relation to the first axis of the head form; generating a rotational acceleration in relation to the first axis when the helmet is installed on the head form; determining a degree of protection against rotational acceleration in relation to the first axis afforded by the helmet; generating a baseline rotational acceleration in relation to the second axis of the head form; generating a rotational acceleration in relation to the second axis when the helmet is installed on the head form; and determining a degree of protection against rotational acceleration in relation to the second axis afforded by the helmet.

In accordance with an aspect of the present invention, there is provided a method for comparing first and second helmets, the method comprising: providing a head form adapted and constrained to rotate separately about a first axis of rotation and a second axis of rotation; generating a rotational acceleration in relation to the first axis when the first helmet is installed on the head form; generating a rotational acceleration in relation to the first axis when the second helmet is installed on the head form; comparing the rotational acceleration in relation to the first axis and the second axis between when the first and second helmets are installed on the head form.

In accordance with an aspect of the present invention, there is provided a method for comparing first and second helmets, the method comprising: i. selecting a first head form adapted and constrained to rotate about a first axis of rotation of a plurality of axes of rotation; ii. installing a first helmet on the first head form; iii. exerting a first force on the first helmet installed on the first head form at a first designated location to thereby cause the first head form to rotate about the first axis of rotation; iv. measuring an indicator of rotational acceleration in relation to the first axis of the first head form; v. determining a rotational acceleration in relation to the first axis of the first head form when the first helmet is installed on the first head form; and vi. installing a second helmet on the first head form; vii. exerting the first force on the second helmet installed on the first head form at the first designated location to thereby cause the first head form to rotate about the second axis of rotation; viii. measuring an indicator of rotational acceleration in relation to the second axis of the first head form; ix. determining a rotational acceleration in relation to the second axis of the first head form when the second helmet is installed on the first head form; and x. comparing the rotational accelerations in relation to the first axis between the first and second helmets; xi. selecting a second head form adapted and constrained to rotate about a second axis of rotation of a plurality of axes of rotation; xii. installing the first helmet on the second head form; xiii. exerting a second force on the first helmet installed on the second head form at a second designated location to thereby cause the second head form to rotate about the second axis of rotation; xiv. measuring an indicator of rotational acceleration in relation to the second axis of the second head form; xv. determining a rotational acceleration in relation to the second axis of the second head form when the first helmet is installed on the second head form; xvi. installing a second helmet on the second head form; xvii. exerting the force on the second helmet installed on the second head form at the second location to thereby cause the second head form to rotate about the second axis of rotation; xviii. measuring an indicator of rotational acceleration in relation to the second axis of the second head form; xix. determining a rotational acceleration in relation to the second axis of the second head form when the second helmet is installed on the head form; xx. comparing the rotational accelerations in relation to the first axis between the first and second helmets.

In accordance with an aspect of the present invention, there is provided an apparatus comprising: at least one head form; a helmet configured for attachment to said at least one head form; an impact delivery unit for delivering an impact force to said helmet at at least one designated location when said helmet is attached to said at least one head form; said at least one head form being selectively rotatable about a plurality of different axes of rotation, wherein movement of said at least one head form is constrained to be able to move only in rotation and only in rotation about one axis of rotation of said plurality of axes at any time; a measuring system for providing an indicator of the acceleration of said at least one head form when rotated about each of said plurality of axes; wherein when said impact delivery unit delivers an impact to said at least one head form, said measurement device associated with each said head form measures the acceleration of each said head form during rotations about each of said plurality of axes of rotation.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In the figures which illustrate embodiments of the invention by example only,

FIG. 23 is a diagram illustrating motion of a head form of the apparatus of FIG. 1;

FIGS. 30A and 30B are diagrams illustrating motion of a head form of the apparatus of FIG. 1.

DETAILED DESCRIPTION

Figure 1:
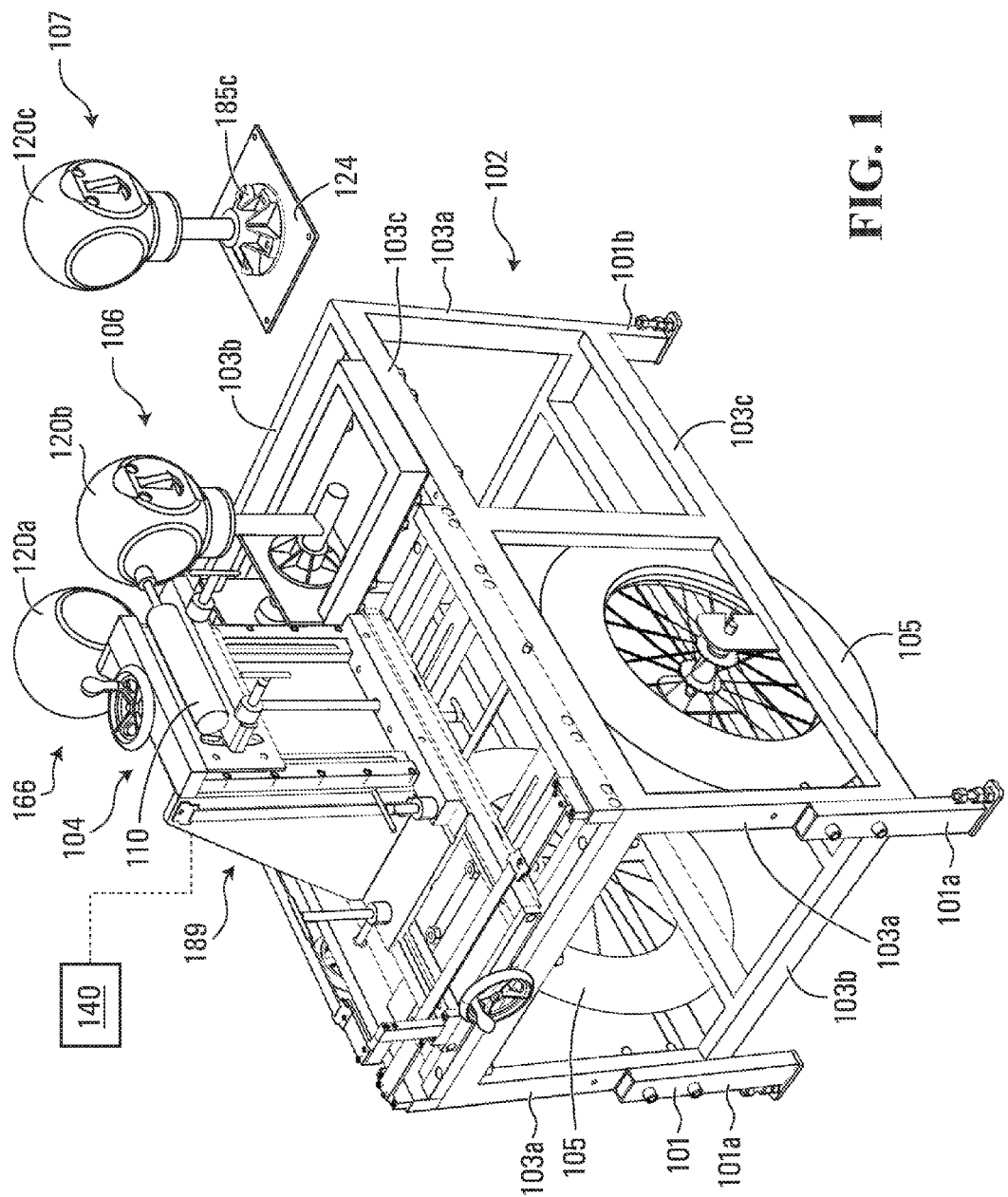
FIG. 1 is a front top perspective view of an apparatus in a first configuration exemplary of an embodiment of the present invention.

With reference to FIGS. 1-19 in which like reference designators refer to like elements, a test apparatus 100 exemplary of an embodiment of the present invention is shown in three configurations, wherein FIGS. 1-9 show apparatus 100 in a first configuration, FIGS. 10-14 show apparatus 100 in a second configuration, and FIGS. 15-19 show apparatus 100 in a third configuration.

As shown, test apparatus 100 may generally comprise a frame 102 formed of a plurality of support frame members 103 arranged substantially in a cuboid shape. Support frame members 103 may be made from one or more suitable materials such as a metal like steel or aluminium, so as to be able to withstand the loads generated by test apparatus 100. Also support members may include generally vertically oriented frame members 103a that are positioned to be able to also maintain test apparatus in a stable orientation and resist any significant movement while test apparatus 100 is being operated. Frame 102 may also include pairs of vertically spaced upper and lower transverse frame members 103b and pairs of vertically spaced upper and lower longitudinal frame members 103c. Together frame members 103a, 103b and 103c are interconnected together by suitable means such as for example nuts and bolts to form a rigid, strong and stable platform for other components of test apparatus 100.

In some embodiments, frame 102 may include pairs of leg extension members 101a, 101b and a pair of wheels 105 mounted for rotation to frame 102 which can provide mobility for test apparatus 100. More specifically, as shown, while leg extension members 101b at one end of apparatus 100 may be just integral extensions of frame members 103a, leg extension members 101a at the opposite end of apparatus 100 may be releasably attached plates that can be connected to the lower portions of frame members 103a in any suitable manner, such as by nuts and bolts. When it is desired to move apparatus 100, leg extensions 101a may be removed from connection with frame members 103a so that a pair of wheels 105 mounted on shafts secured to frame 102, may be lowered into contact with the floor surface. The opposite end of apparatus 100 may then be lifted so that the most of the weight of apparatus 100 can be taken by the wheels 105. Test apparatus 100 can thus be made mobile when it is desired to move test apparatus 100 from one location to another. When test apparatus 100 is to be operated, frame 102 may be configured with leg extensions 101a, 101b engaging the ground to provide a stable base for test apparatus 100.

Mounted to frame 102 may be two separate units: (1) an impact delivery unit generally designated as 199 and (2) a head form assembly unit 166.

Impact delivery unit 199 may include a piston assembly unit 104 mounted to the frame 102. Head form assembly unit 166 may include head form assemblies 106, 107 which may be interchangeably mounted to the frame 102. Head form assemblies 106, 107 may comprise three separate head forms 120a, 120b and 120c. Head forms 120a, 120b, and 120c may respectively each have a measurement device for measuring acceleration, such as accelerometers 142a, 142b, 142c (see for example FIGS. 20A-20C and collectively designated as accelerometers 142). Impact delivery unit 199 including a piston assembly unit 104, as well as head form assembly 166, may be configured on frame 102 and positioned in relation to each other, in such a manner that a force actuator (e.g. a piston device) 110 of piston assembly unit 104 is able to exert impact forces on head forms 120a, 120b and 120c of head form assemblies 106, 107 as described in detail hereinafter.

Test apparatus 100 also includes a measuring system consisting of a data acquisition device 140 (FIG. 1) and suitable electronics, such as electrical wiring or a wireless transmitter, for communicating signals from accelerometers 142 disposed within the head form assemblies 106, 107 to data acquisition device 140 for processing, also as described below.

Figure 3:
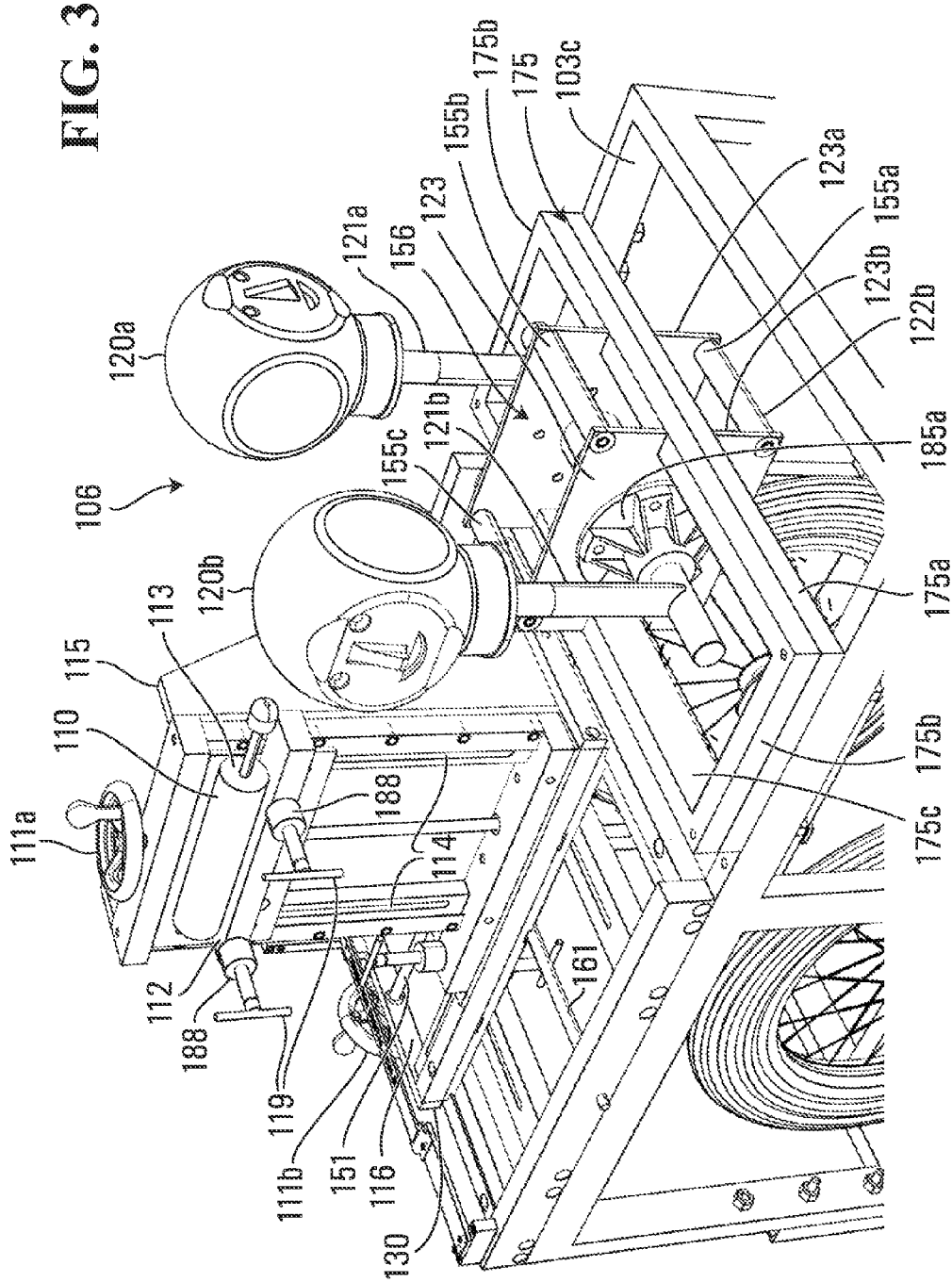
FIG. 3 is an enlarged partial front top perspective view of the apparatus of FIG. 1 in the first configuration.
Figure 4:
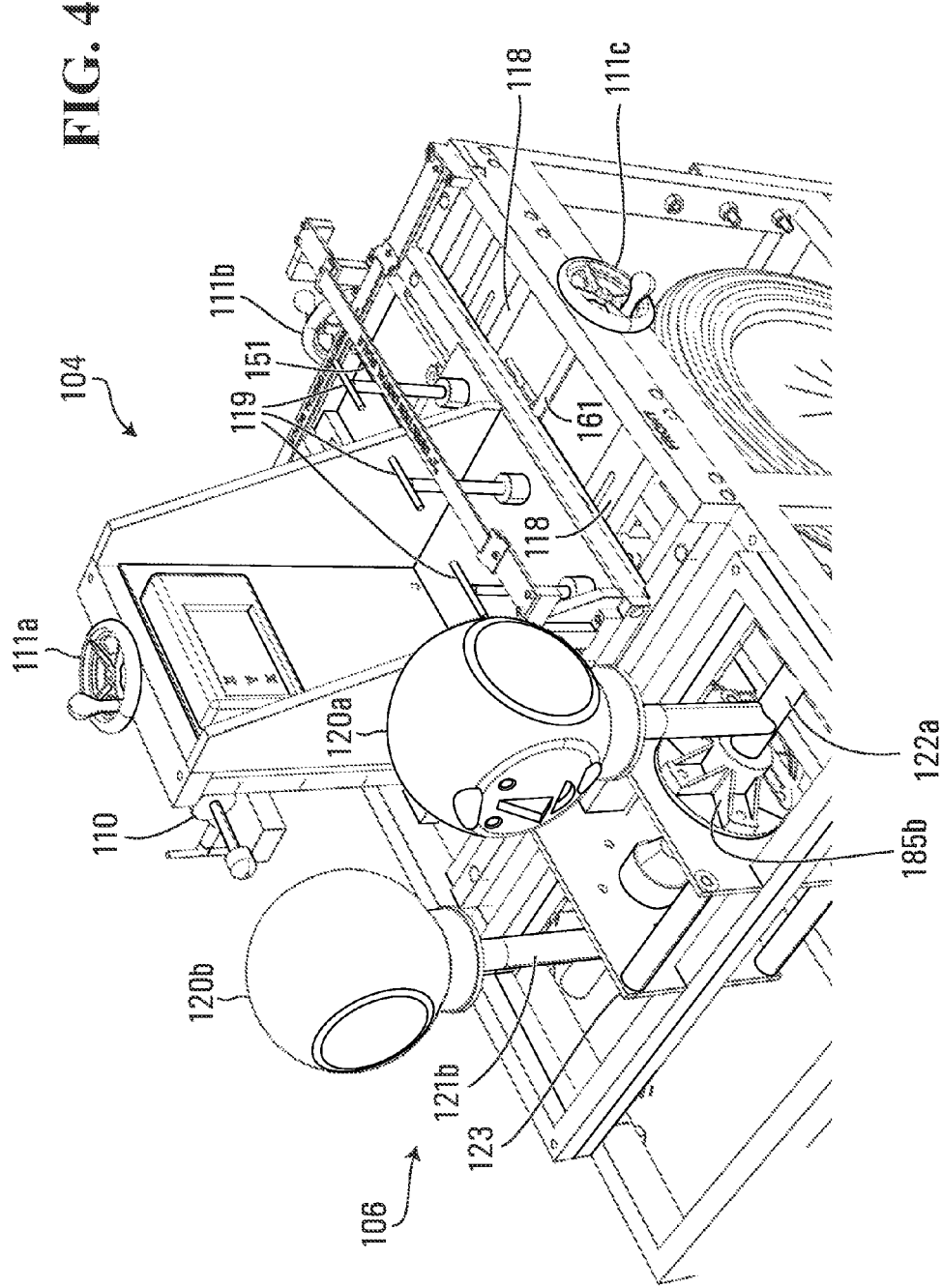
FIG. 4 is an enlarged partial rear top perspective view of the apparatus of FIG. 1 in the first configuration.

As best shown in FIGS. 3 and 4, head form assembly 106 may include first and second head forms 120a, 120b with each being mounted on a respective neck attachment member 121a, 121b. Each neck attachment member 121a, 121b may be attached to a respective freely rotatable shaft 122a, 122b with each shaft 122a, 122b being freely rotatably mounted to a respective bearing housing 185a, 185b containing a bearing to retain the shafts 122a, 122b, and permit the free rotation of the shafts 122a, 122b. Each bearing housing 185a, 185b is mounted to one of two opposed vertically and longitudinally oriented base plates 123a, 123b. As shown, base plates 123a, 123b may be interconnected to each other with transversely oriented tubular support members 155a-d to form a rigid base support unit 156 that may be supported on and releasably attachable to a rigid rectangular support frame unit 175. Frame unit 175 may have longitudinally oriented members 175b that are configured to rest on top of and be aligned with frame members 103c. Frame unit 175 may also include cross members 175a that span across frame members 103c. Base plates 123a, 123b, may each be provided with notches to provide flanges that allow the base unit 156 to rest upon top of and be secured to frame 175. Base unit 156 can be secured to frame 175 using nuts and bolts or other suitable means. Although it may be possible to remove base unit from frame 175 in some embodiments, base unit 156 is not intended to be removed from frame unit 175 during normal operations. Interchange of neck attachments is done by exchanging or moving frame units 175 with a base unit attached. Frame unit 175 may be secured to frame members 103c of frame 102 in any suitable manner, such as by nuts and bolts.

As can be appreciated, head form 120a is adapted to simulate rotational neck movement in the direction of a sagittal plane (such as mid-sagittal plane P1 in FIG. 20A) about the shaft 122a that is oriented and rotates about an axis A1 (FIG. 14) that is perpendicular to such a sagittal plane of head form 120a. Similarly head form 120b is adapted to simulate rotational neck movement in the direction of a coronal plane (such as the mid-coronal plane P2 in FIG. 20B) about the shaft 122b that is oriented and rotates about an axis A2 (FIG. 7) of head form 120b.

Head forms 120a, 120b may be held in the near vertical orientation shown in FIGS. 1 to 14 by any suitable mechanism. For example, as illustrated only in FIGS. 2 and 30A,B in relation to head form 120a, a steel plate 174 may have one end attached to shaft 122a by welding or other known attachment mechanisms, and positioned such that in the orientation shown in FIGS. 2 and 30A, the opposite end of plate 174 is able to abut against a cross member 175a of frame unit 175, thus allowing head form 120a to rest in a near vertical orientation and slightly leaned towards piston 110. Impacts may be kept perpendicular by elevating the vertical angle of piston 110 slightly to compensate for the slight lean of head form 120a. As will now be appreciated, subsequent to impact plate 174 will be lifted away from cross member 175a due to rotation of head form 120a, as shown in FIG. 30B. A similar mechanism may be used to hold head form 120b in the near vertical orientation shown in FIGS. 1 to 14.

While head forms 120a and 120b are shown to share a single common base unit 156, it will be appreciated that head forms 120a and 120b may be constructed separately with each head form 120a, 120b having its own base unit so that each head form 120a, 120b may be individually and separately mounted to frame 102.

Figure 15:
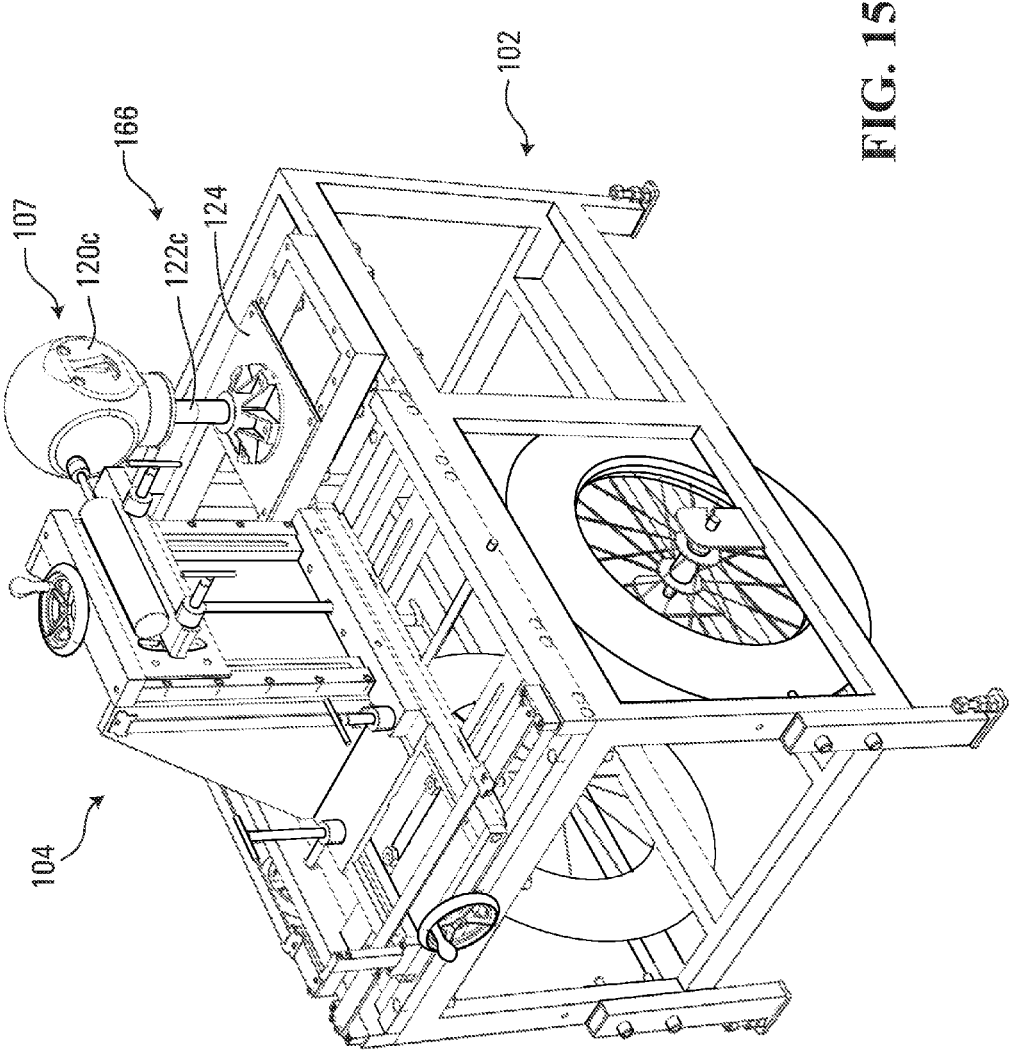
FIG. 15 is a front top perspective view of the apparatus of FIG. 1 in a third configuration.
Figure 16:
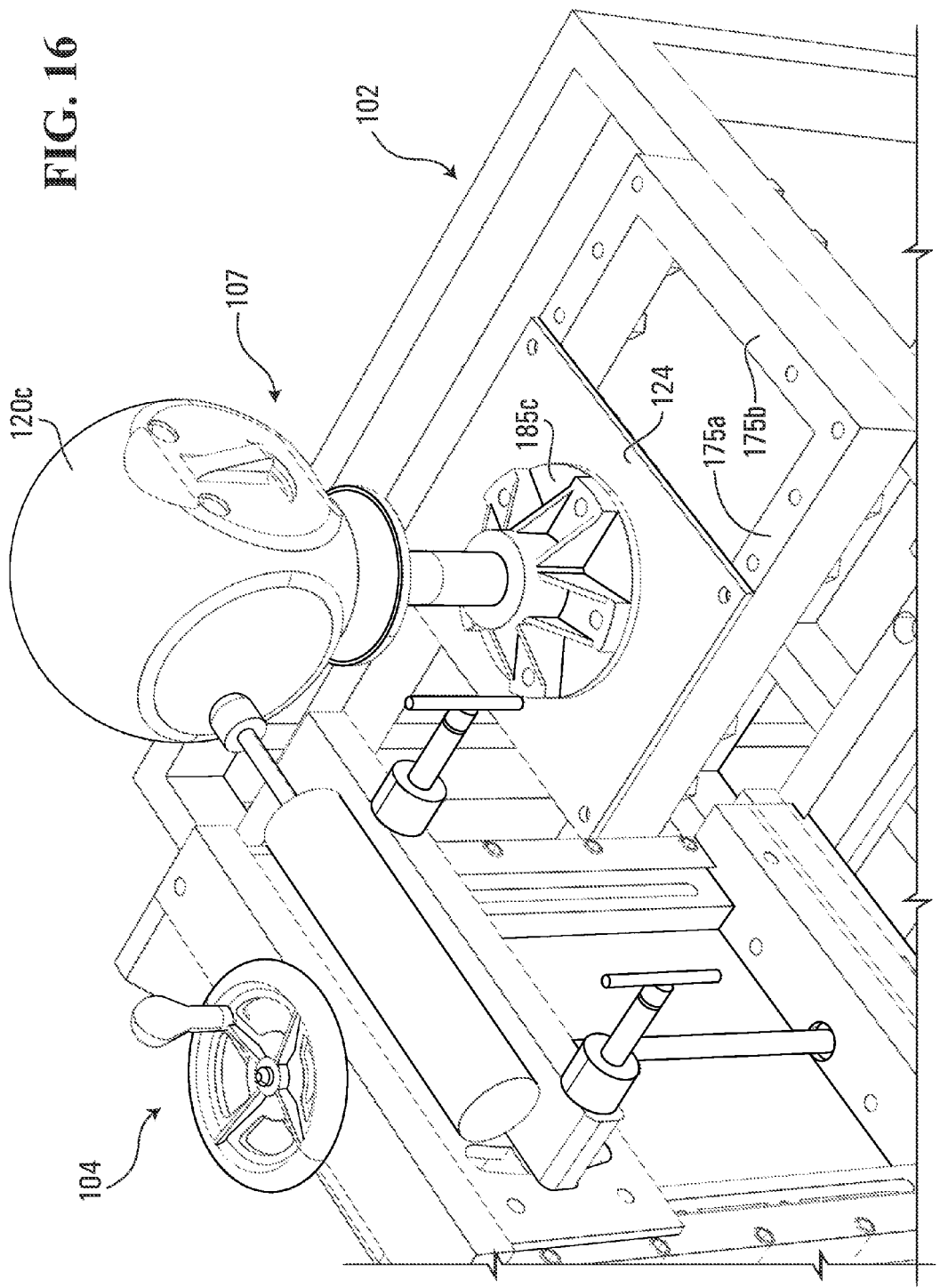
FIG. 16 is an enlarged partial front top perspective view of the apparatus of FIG. 1 in the third configuration.
Figure 17:
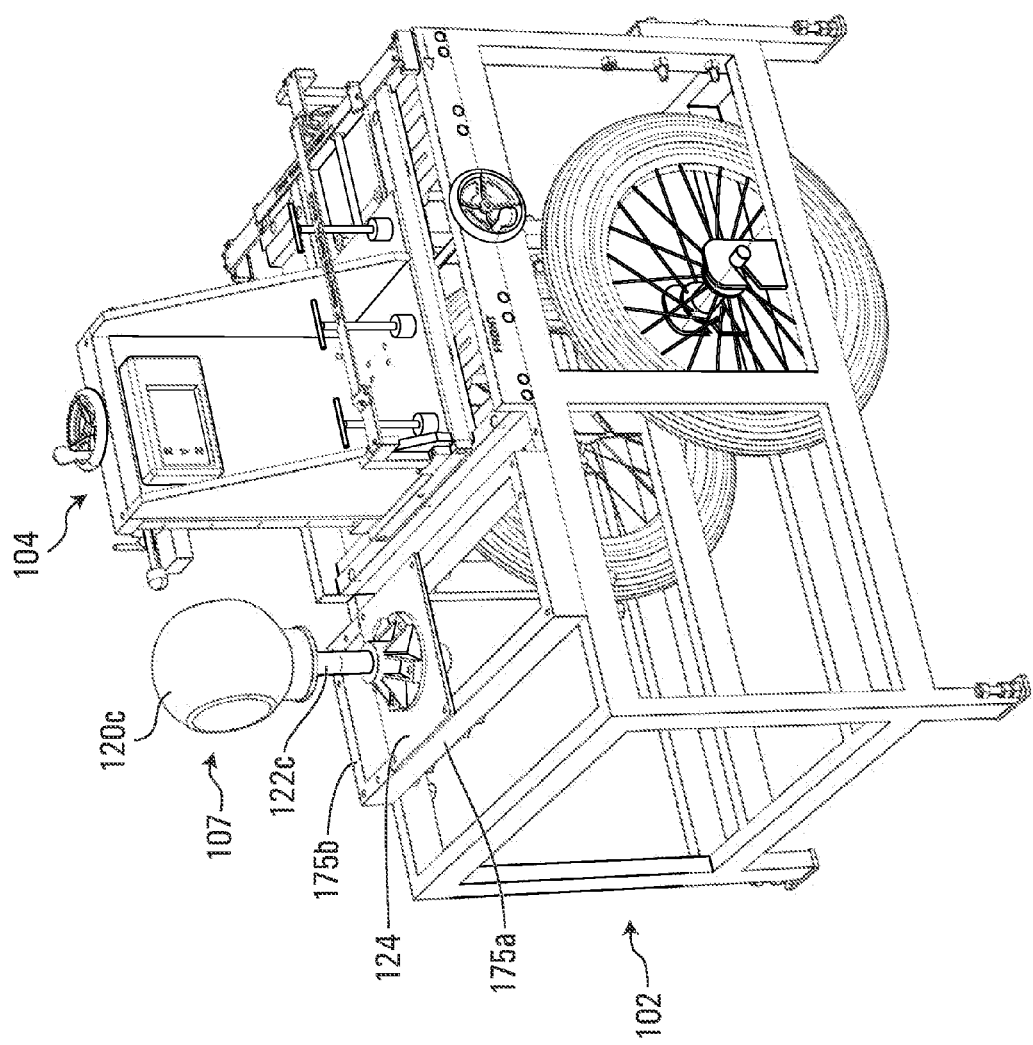
FIG. 17 is a rear top perspective view of the apparatus of FIG. 1 in the third configuration.
Figure 18:
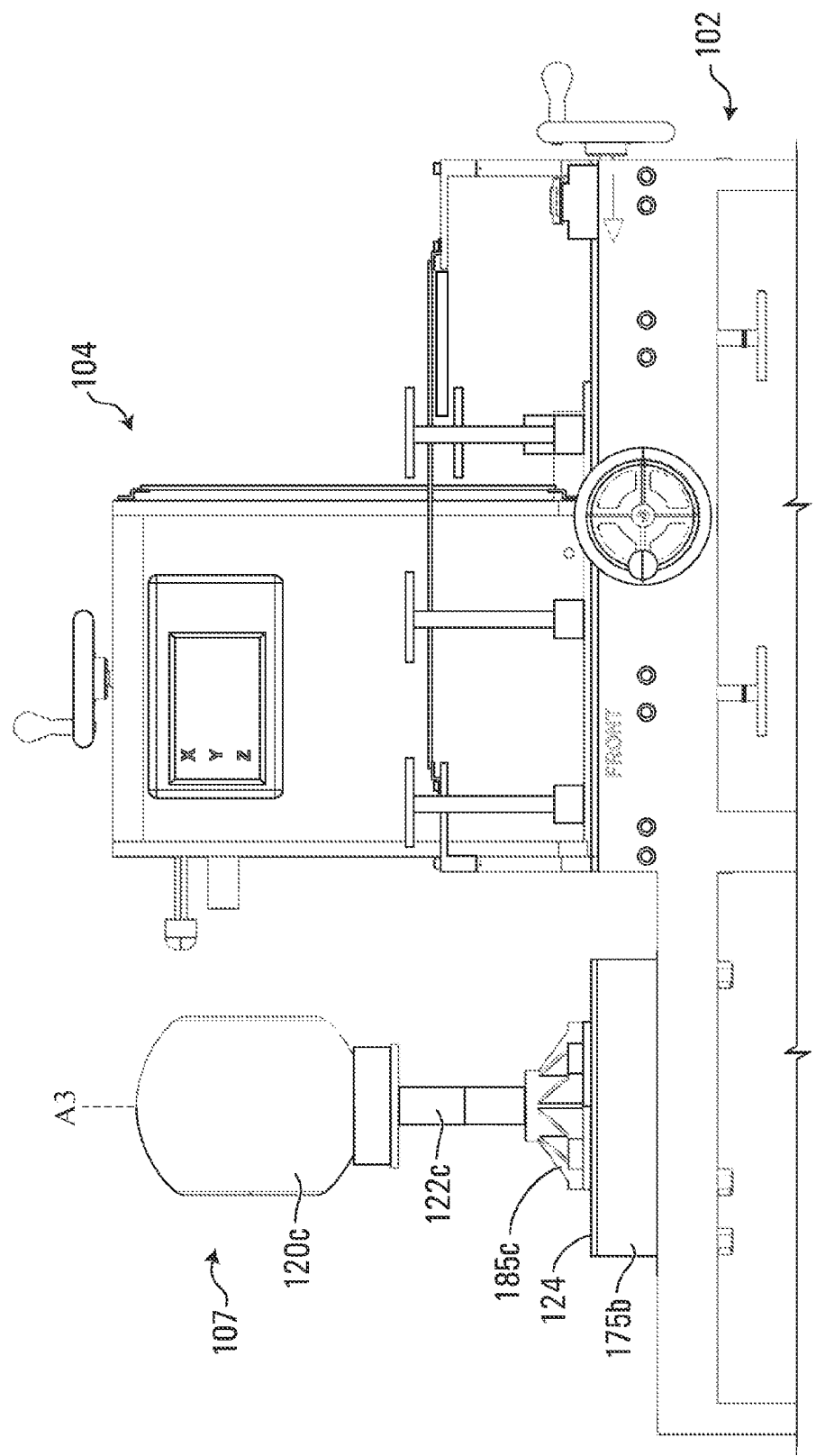
FIG. 18 is an enlarged partial rear view of the apparatus of FIG. 1 in the third configuration.
Figure 19:
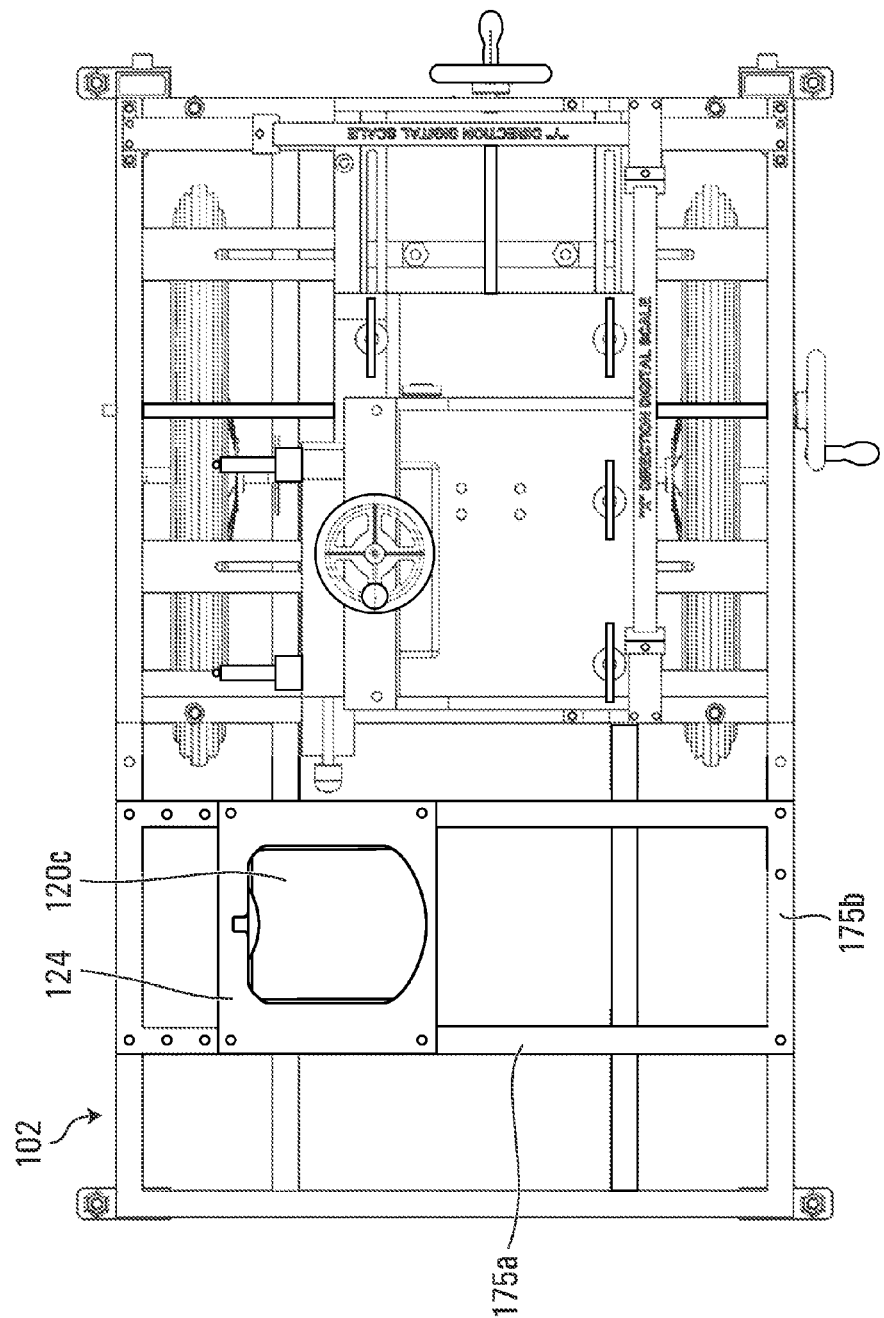
FIG. 19 is a top view of the apparatus of FIG. 1 in the third configuration.

As best shown in FIG. 15, the other head form assembly 107 may include a single head form 120c mounted on a shaft 122c, with shaft 122c being freely rotatably mounted to a respective bearing housing 185c containing a bearing to retain the shaft 122c and permit the free rotation of the shaft 122c. Bearing housing 185c may be suitably mounted such as with nuts and bolts to a base plate 124. Base plate 124 may be removably attached to the same rigid rectangular frame 175 as unit 156 can be attached to. Alternatively head form assembly 107 may utilize an alternate rectangular frame constructed like frame 175, to enable the head form assembly 107 to be releasably secured to rectangular support frame 175 using any suitable manner, such as by nuts and bolts. As can be appreciated, head form 120c is adapted to simulate rotational neck movement in an axial plane (such as axial plane P3 in FIG. 20C) about the shaft 122c that is oriented and rotates about a vertical axis A3 (see FIG. 18) that is perpendicular to such an axial plane of head form 120c. Head form 120c is positioned with face anterior prior to each impact as shown in FIG. 15. The rotation of head form 120c about the vertical axis (in or in alignment with an axial plane) is unconstrained.

Head forms 120a, 120b, 120c (collectively, head forms 120) may be sized and shaped to simulate a human head and, as described in more detail below, head forms 120 are adapted to receive various types of helmets for testing. Each head form 120 may be, for example, A NOCSAE (National Operating Comittee on Standards for Athletic Equipment) standard anthropometric humanoid head form, medium size, corresponding to an average adult head.

Figure 20A:
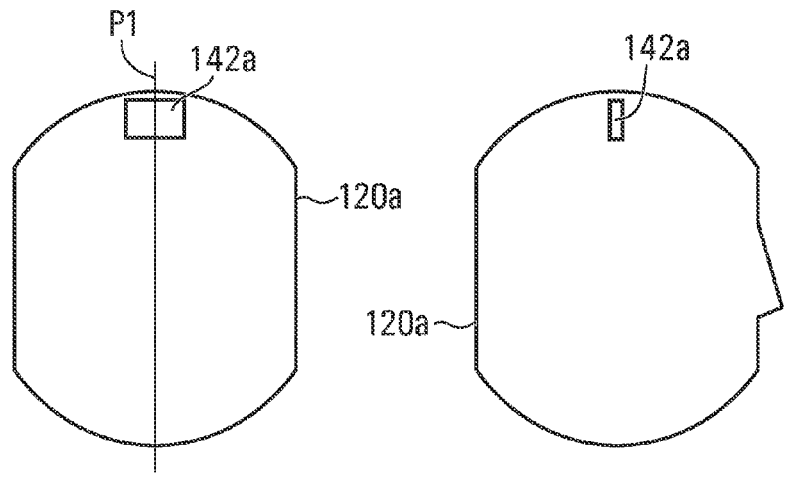
FIG. 20A is a diagram of a head form of the apparatus of FIG. 1.
Figure 20B:
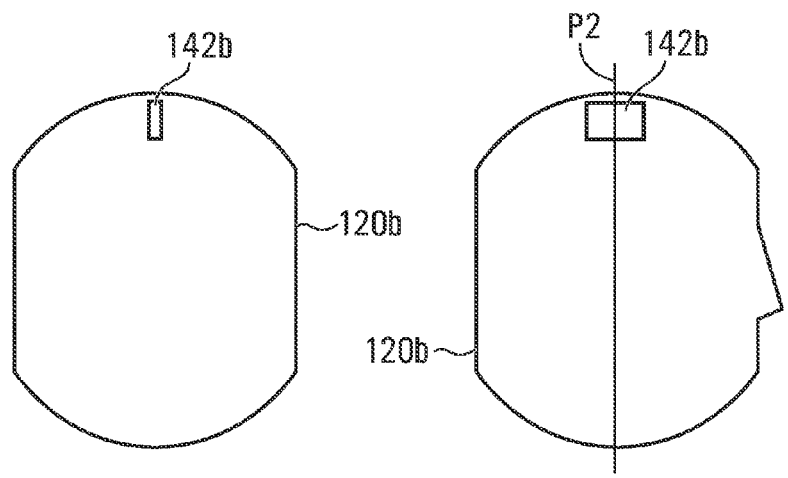
FIG. 20B is a diagram of a head form of the apparatus of FIG. 1.
Figure 20C:
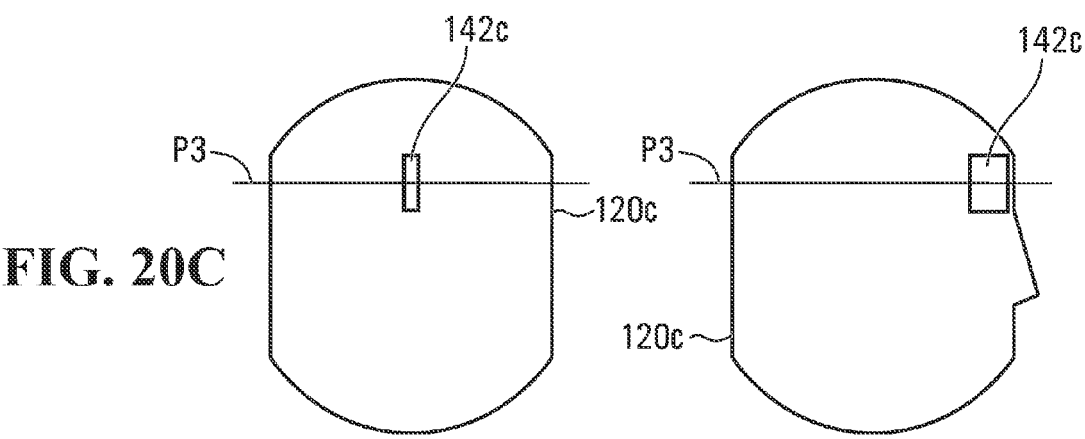
FIG. 20C is a diagram of a head form of the apparatus of FIG. 1.

As shown in FIGS. 20A-20C, disposed within head forms 120 may be accelerometers 142 for measuring acceleration in head forms 120. Apparatus 100 may include suitable electronics, such as electrical wiring, or a wireless transmitter, for communicating signals from accelerometers 142 to data acquisition device 140 that is adapted to receive the signals and then conduct the processing of the data contained in the signals. In some embodiments accelerometers 142 are standard uni-axial digital accelerometers, such as Model 2260-100 accelerometers manufactured by Silicon Designs Inc. having a differential output range of +/−4V and a sensitivity of 40 mV/g. Though each head form 120 is shown having only one accelerometer 142, it will be appreciated that additional accelerometers may be used for obtaining acceleration measurements. Data acquisition device 140 may be, for example, a computer having a USB-1208LS digital I/O module manufactured by Measurement Computing Corporation connected thereto. Accelerometers 142 are operable to be able to measure a linear acceleration imparted in a particular linear direction. When mounted in the head form, the accelerometer may be positioned so that it measures the linear acceleration in a direction that is aligned with its respective direction of rotational motion. For example, as shown in FIGS. 20A, 20B, 20C, each accelerometer 142a, 142b, 142c is aligned with one of the respective planes P1, P2 or P3 of rotation of its corresponding head form 120a, 120b, 120c. As shown, each accelerometer 142 may be positioned to correspond to a point of maximum tangential linear acceleration of its corresponding head form 120. Thus, for axial rotation accelerometer 142c may be positioned in the forehead region of head form 120c, whereas for sagittal and coronal rotations, accelerometers 142a and 142b may be positioned in the crown region of head forms 120a and 120b, respectively.

Having described the head form assembly unit 166, the impact delivery unit generally designated as 199 is now described. Impact delivery unit 199 may include a force actuator, such as a pneumatic piston device 110, mounted to a positioning and support apparatus 189.

Piston device 110 may be a standard pneumatic piston device configured to propel a piston housed in a cylinder outwardly in an axial direction at a predetermined rate of acceleration. For example, piston device 110 may include a PARKER pneumatic cylinder with a 2.00 inch bore housing a stainless steel piston with a 6.00 inch stroke length, with model number 2.00DSRY06.00 that can be propelled forward by air pressure. A stainless steel impacting weight, weighing 1.3 kg may be attached to the end of the piston may be used as an impact surface and may provide a increased mass to enhance the impact force exerted by the piston. Compressed air to drive the piston may be supplied from a compressor (not shown), and the motion of the piston may be controlled by a dual action unrestricted flow valve (not shown) which, when activated using an electrical switch (not shown), causes the piston to be propelled forward and subsequently retract.

Positioning and support apparatus 189 may be configured to support piston device 110 and may be operable to move the position and orientation of piston device 110 relative to the head forms 120 of head form assembly unit 166 when the head forms 120a, 120b, 120c are in turn mounted to frame 102.

Figure 2:
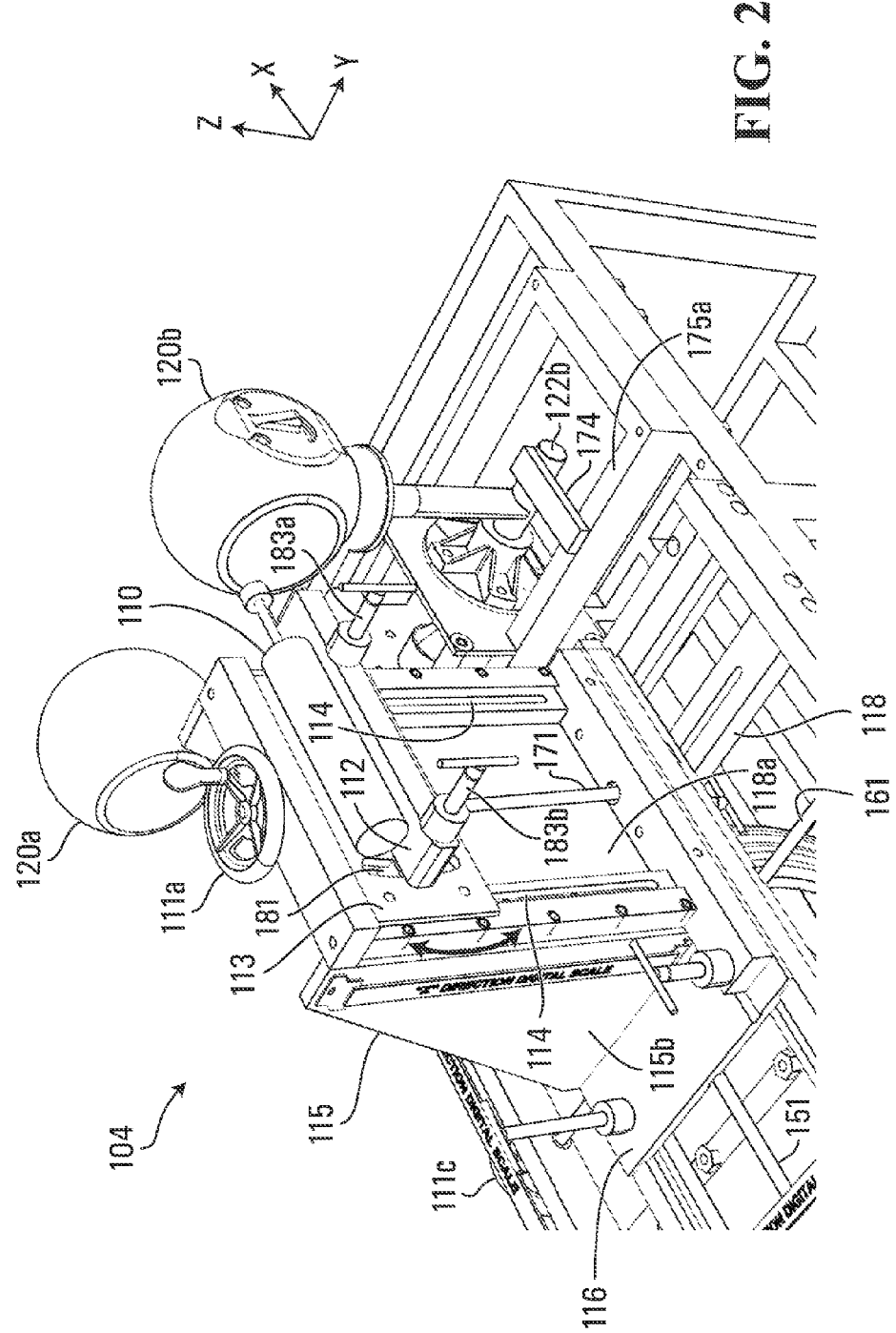
FIG. 2 is an enlarged partial front top perspective view of the apparatus of FIG. 1 in the first configuration.

Positioning and support apparatus 189 will now be described with particular reference to FIGS. 2, 3 and 7. As shown, positioning apparatus 189 includes an angle alignment support plate 112 to which piston device 110 is mounted with nuts and bolts or other known attachment mechanisms. Angle alignment plate 112 is pivotally mounted to a height (z-direction) alignment plate 113. More specifically, plate 112 is pivotally connected at one end to a shaft 183a passing through a transverse aperture in the plate 112. Shaft 183a is fixed against translational movement relative to plate 113, but permits plate 112 to be able to pivot around shaft 183a relative to plate 113. Plate 112 is connected at an opposite end to a shaft 183b that passes through another transverse aperture in plate 112. Shaft 183b has a first end extending out from plate 112 and an opposite end that is received into a curved slot 181 through plate 113. Thus plate 112 with piston 110 mounted thereto can pivot about a transverse axis in the Y-direction so that the vertical angle of piston 110 can be varied.

An inner end of each shaft 183a, 183b may be received in respective height alignment tracks 114 mounted to a longitudinally and vertically oriented surface 115a of a piston support structure 115 of the positioning apparatus 189 to allow the vertical direction Z position of plates 113, 112 and piston 110 to be adjusted. Piston support structure 115 may include a hand crank 111a attached to a threaded rod 171. Threaded rod 171 may be fed through a threaded block (not shown) affixed to a rear surface of plate 113. By manual adjustment of crank 111a the position of height alignment plate 113 in the vertical Z direction along height alignment tracks 114 can be varied.

Figure 31:
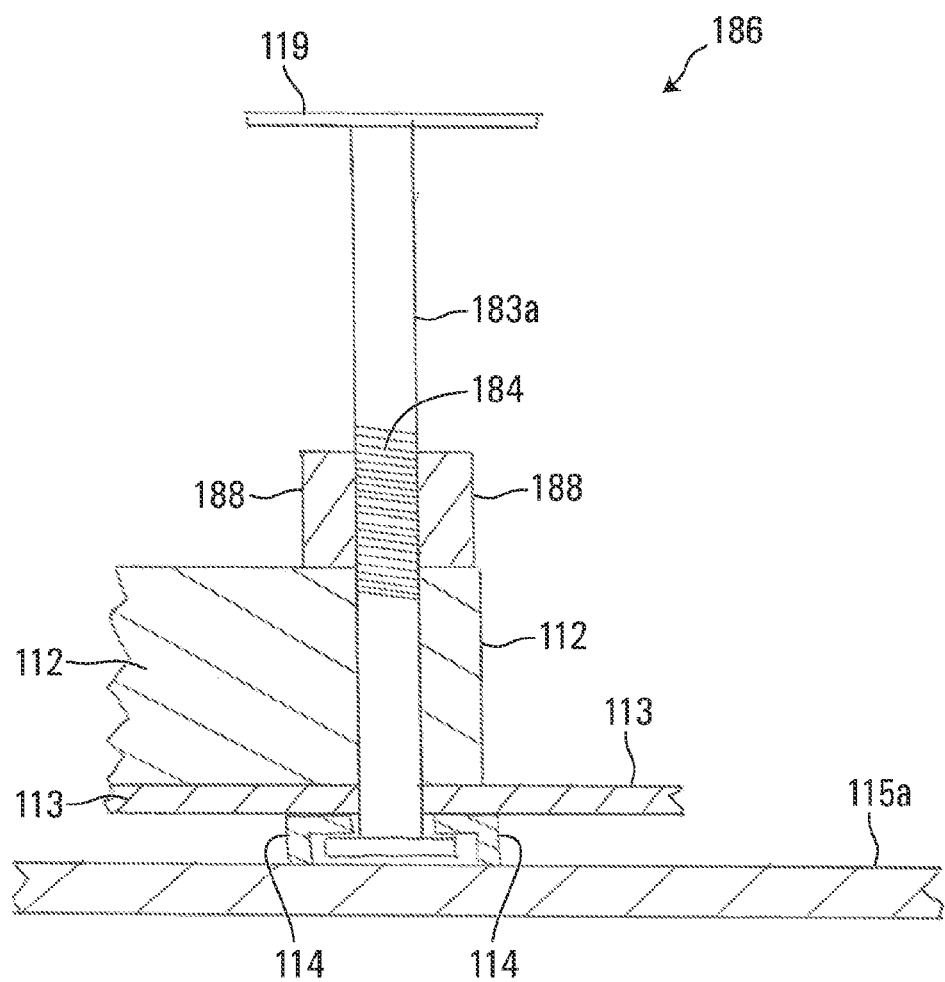
FIG. 31 is a partial cutaway cross-sectional view of an interconnection mechanism of the apparatus of FIG. 1.

FIG. 31 is a cross-section view illustrating an exemplary interconnection mechanism 186 that may be used to interconnect plate 113 and tracks 114 in a manner that allows both for sliding movement of plate 113 on tracks 114 and for securing the position of plate 113 relative to tracks 114. As shown, an inner end of shaft 183a is disposed with a flange 182 adapted to slide inside a track 114 and to hold the inner end of shaft 183a inside the track 114. Shaft 183a passes through apertures in plates 113 and 112, and terminates at an outer end disposed with a handle 119. Shaft 183a has a threaded portion 184 around which a threaded nut 188 (see also FIG. 3) is received. Threaded nut 188 may be manually tightened such that nut 188 will exert a force against plate 112 to thereby hold plate 112 against plate 113 and plate 113 against tracks 114. Thus, interconnection mechanism 186 may be used for releasably securing the angular position of plate 112 and piston 110 relative to plate 113 as well as the vertical position of plates 113, 112 and piston 110 along tracks 114. It will be appreciated however that the configuration and interconnection of plate 113 and tracks 114 may be accomplished by any other suitable mechanism that allows for sliding movement of the plate 113 on tracks 114.

Positioning apparatus 189 also includes a longitude (x-direction) alignment plate 116 slidably mounted to x-direction tracks 117 and a hand crank 111b attached to a threaded rod 151. The configuration and connection between plate 116 and tracks 117 can be similar or the same as that with plate 113 and tracks 114. Piston support structure 115 is mounted to longitude alignment plate 116, which as shown may be in a generally transverse and longitudinal orientation. Threaded rod 151 may be fed through a threaded block (not shown) affixed to a bottom surface of alignment plate 116. This allows manual adjustment of the position of longitude alignment plate 116 along the x-direction tracks 117.

Positioning apparatus 189 also includes a latitude (y-direction) alignment plate 130 slidably mounted to y-direction tracks 118 and a hand crank 111c attached to a threaded rod 161. The configuration and connection between plate 130 and tracks 118 can be similar or the same as that with plate 113 and tracks 114. Tracks 117 are mounted to latitude alignment plate 130. Threaded rod 161 may be fed through a threaded block (not shown) affixed to a bottom surface of alignment plate 130. This allows manual adjustment of the position of latitude alignment plate 130 along the y-direction tracks 118. Tracks 118 are mounted to frame 102.

As will now be appreciated, piston assembly 104 is adapted such that the x-, y- and z-direction coordinates of piston 110 may be manually adjusted using hand cranks 111a,111b,111c (collectively, hand cranks 111), and the vertical angle of piston 110 may be manually adjusted by pivoting angle alignment plate 112 relative to height alignment plate 113. Although in this embodiment the horizontal angle of piston 110 is not adjustable, in other embodiments it would be possible to have this angle be adjustable instead of or in addition to the vertical angle. A plurality of manual clamps 119 (FIGS. 4, 8 and 10) are manually operable to secure the various alignment plates in position once an adjustment is complete, for example by a mechanism similar to interconnection mechanism 186 hereinbefore described in relation to plates 112, 113 and alignment tracks 114.

Figure 5:
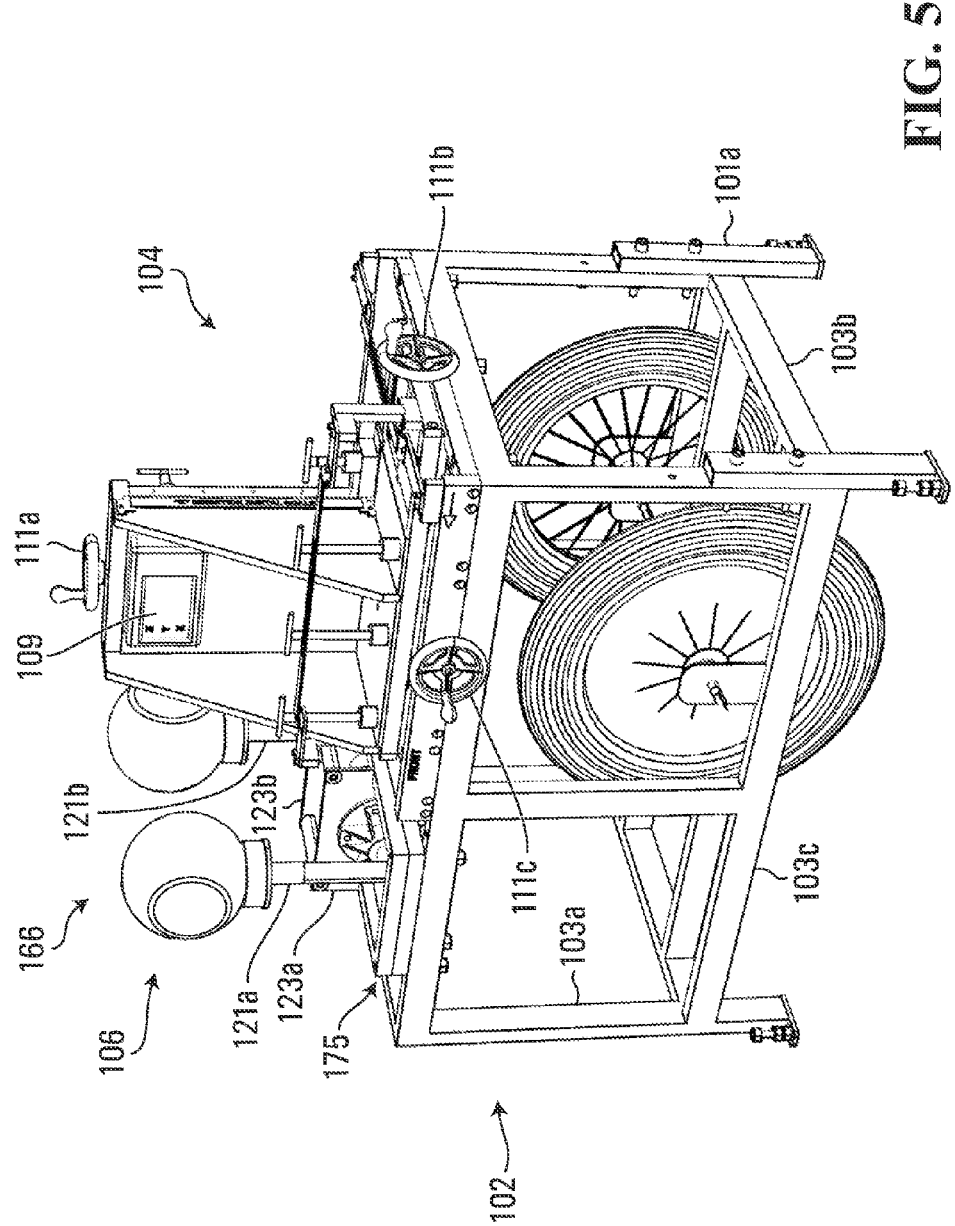
FIG. 5 is a rear top perspective view of the apparatus of FIG. 1 in the first configuration.
Figure 6:
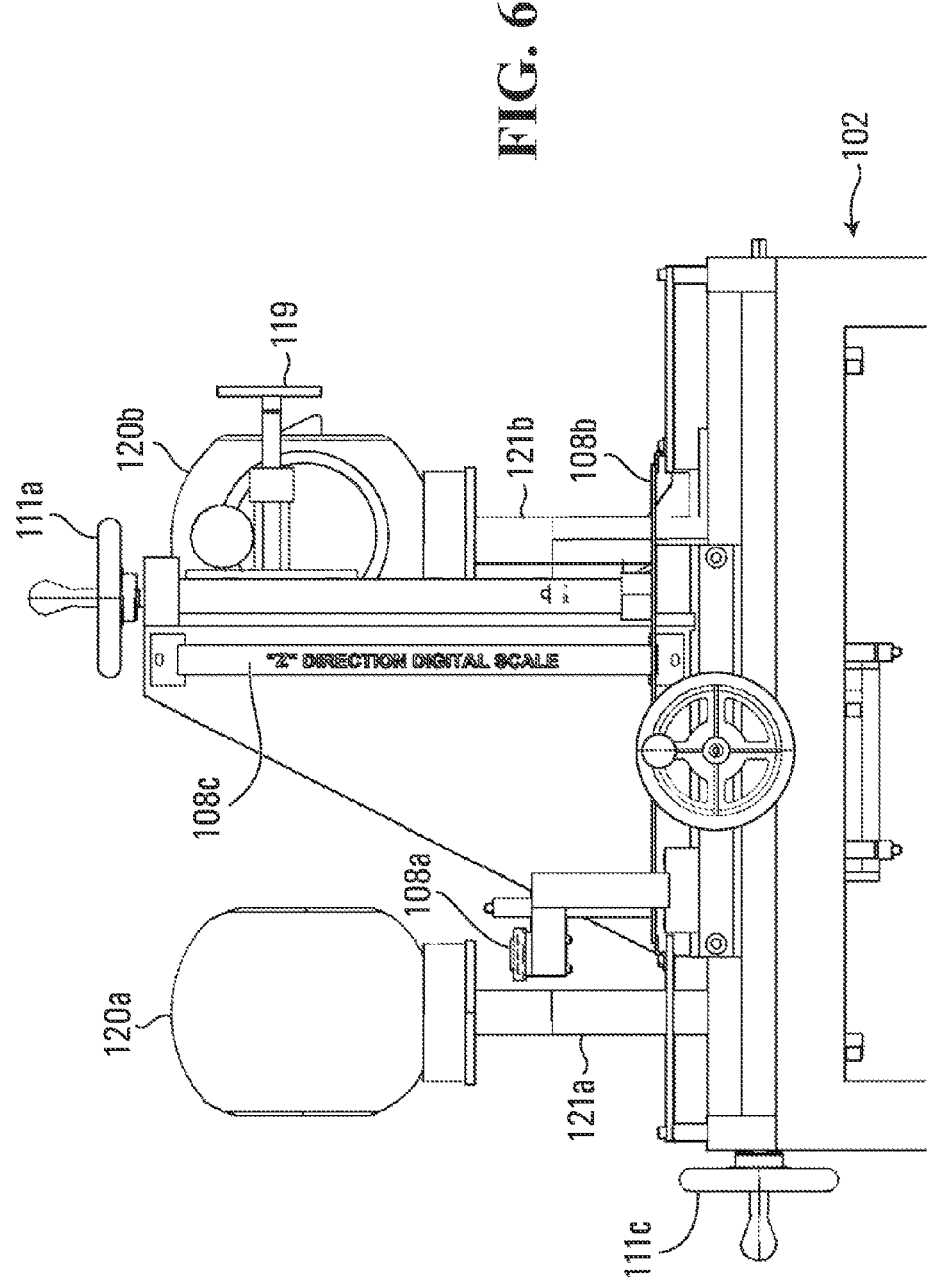
FIG. 6 is an enlarged partial side view of the apparatus of FIG. 1 in the first configuration.
Figure 7:
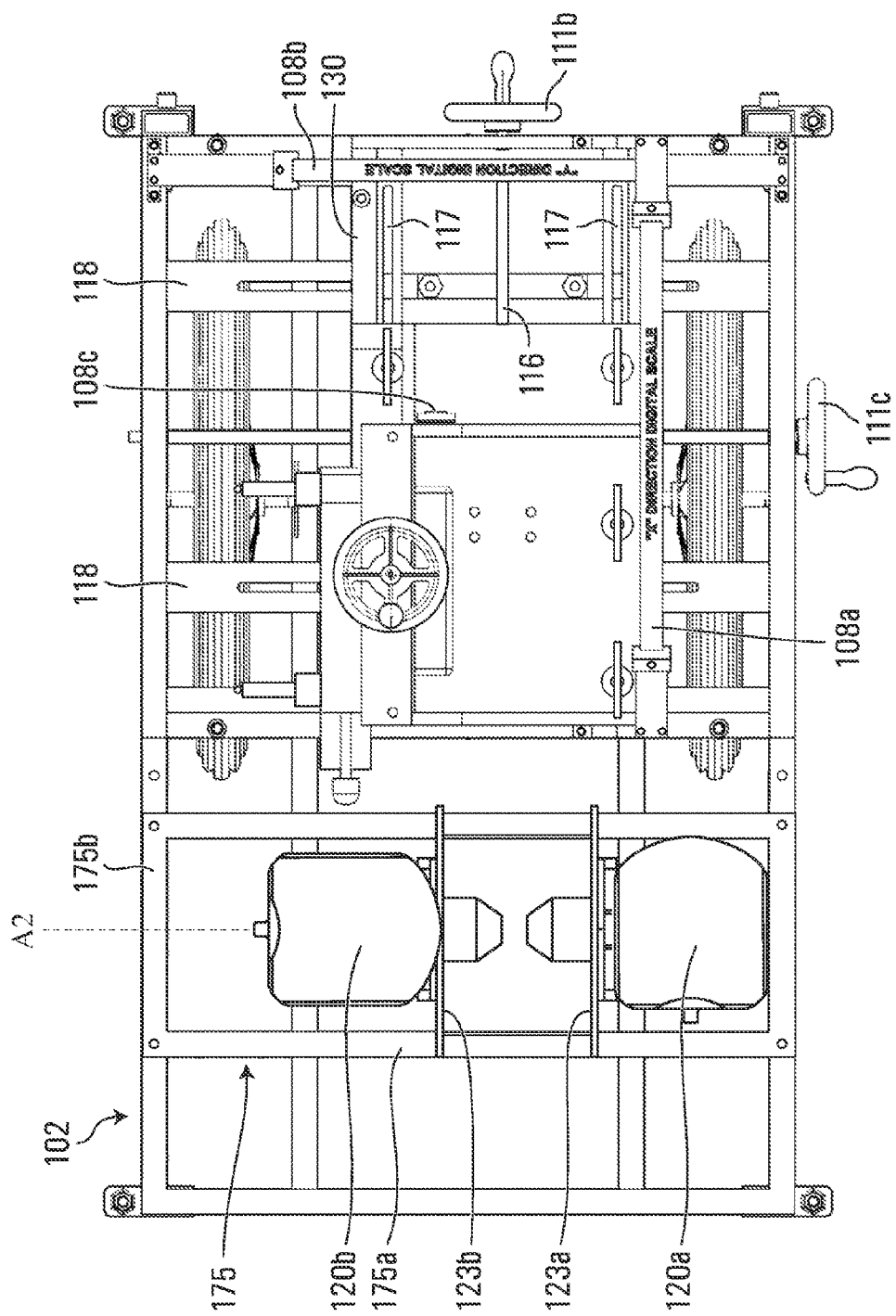
FIG. 7 is a top view of the apparatus of FIG. 1 in the first configuration.
Figure 8:
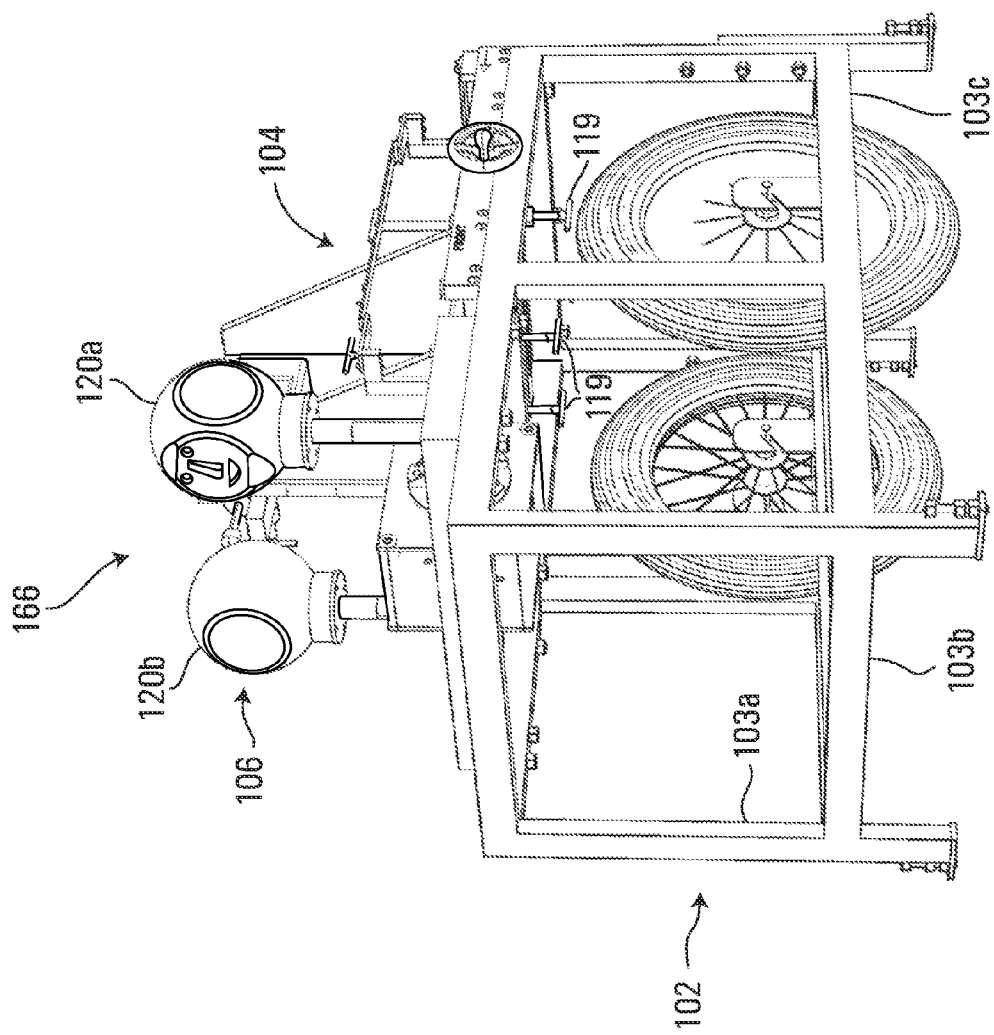
FIG. 8 is a rear side perspective view of the apparatus of FIG. 1 in the first configuration.
Figure 9:
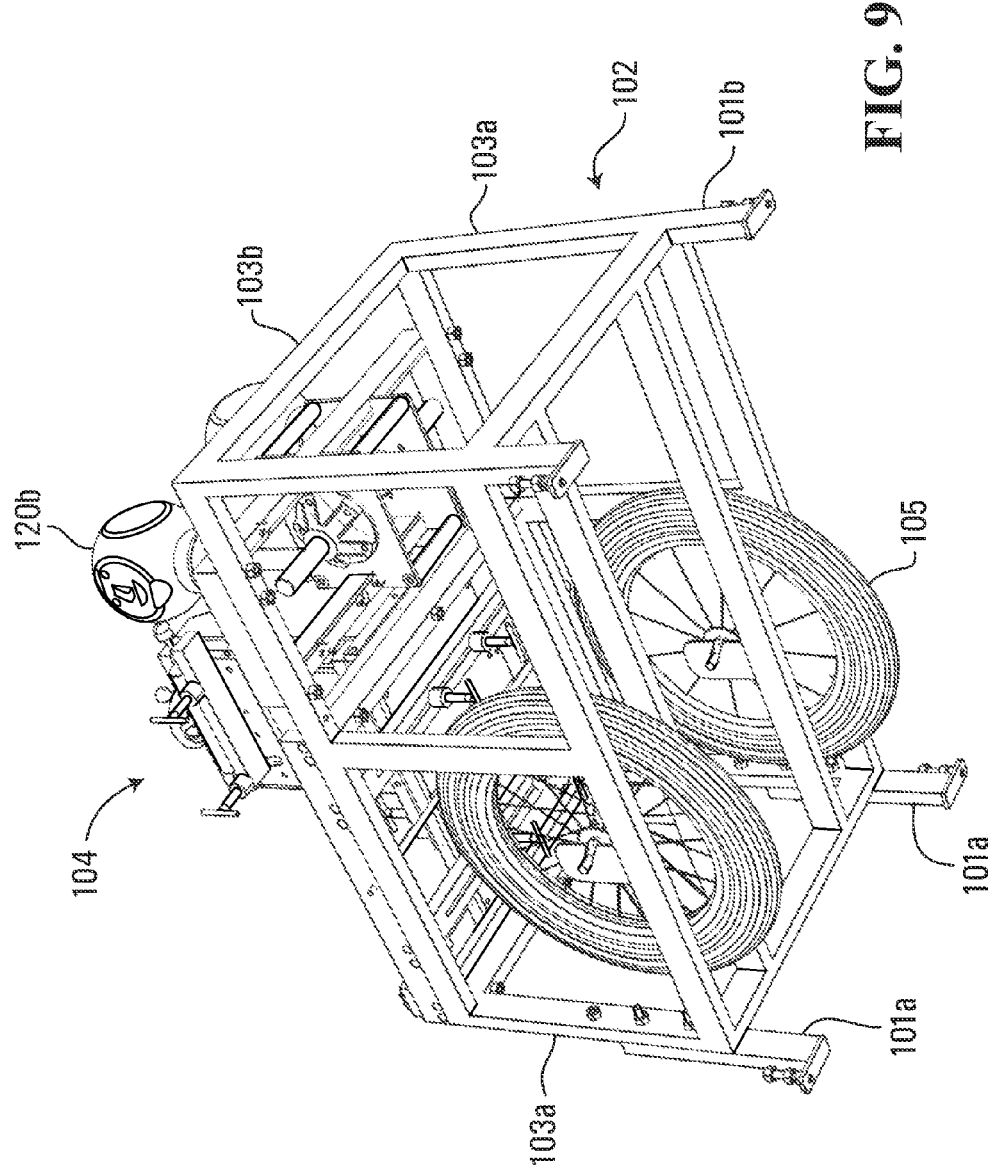
FIG. 9 is a front bottom perspective view of the apparatus of FIG. 1 in the first configuration.
Figure 10:
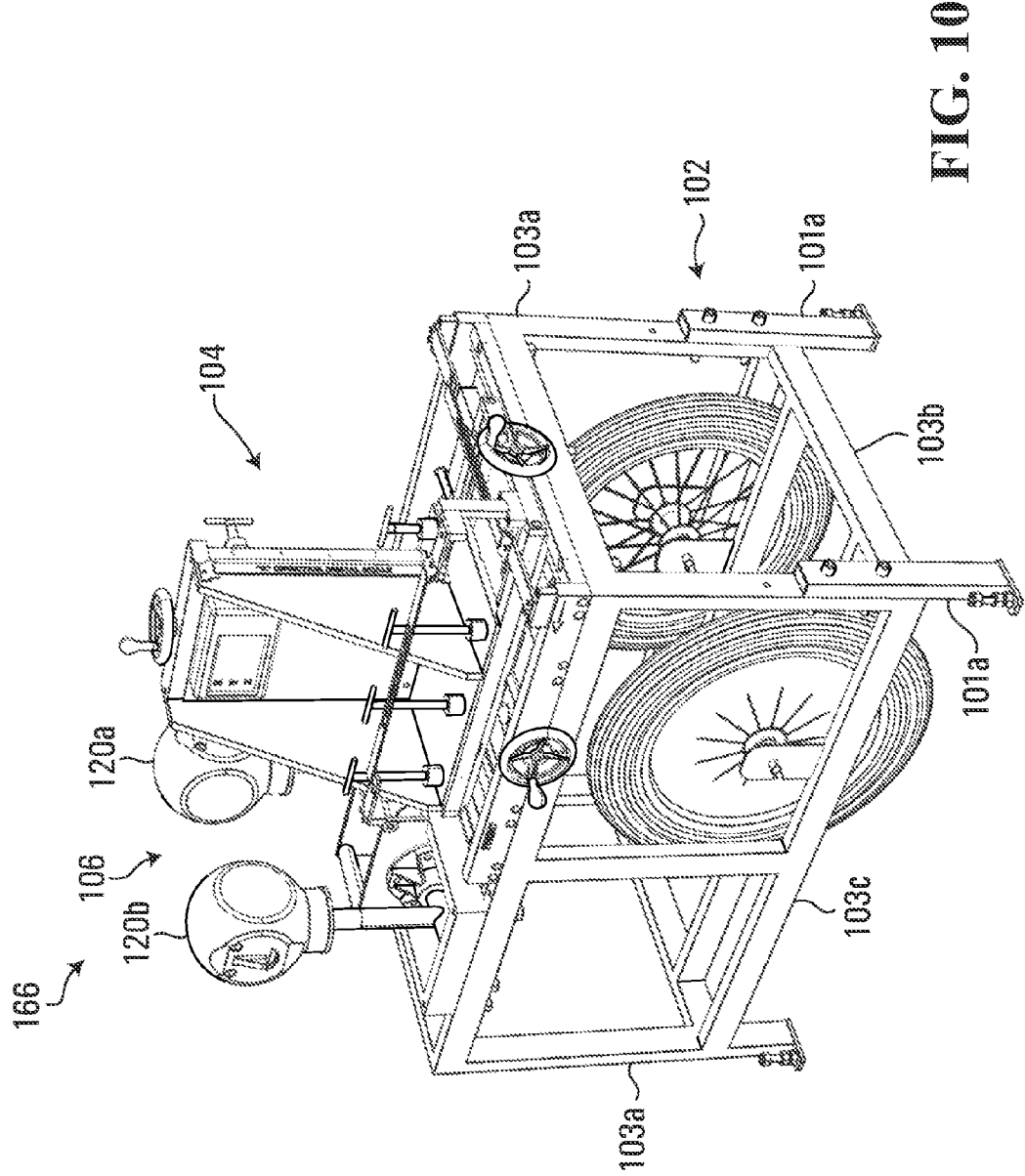
FIG. 10 is a rear top perspective view of the apparatus of FIG. 1 in a second configuration.
Figure 11:
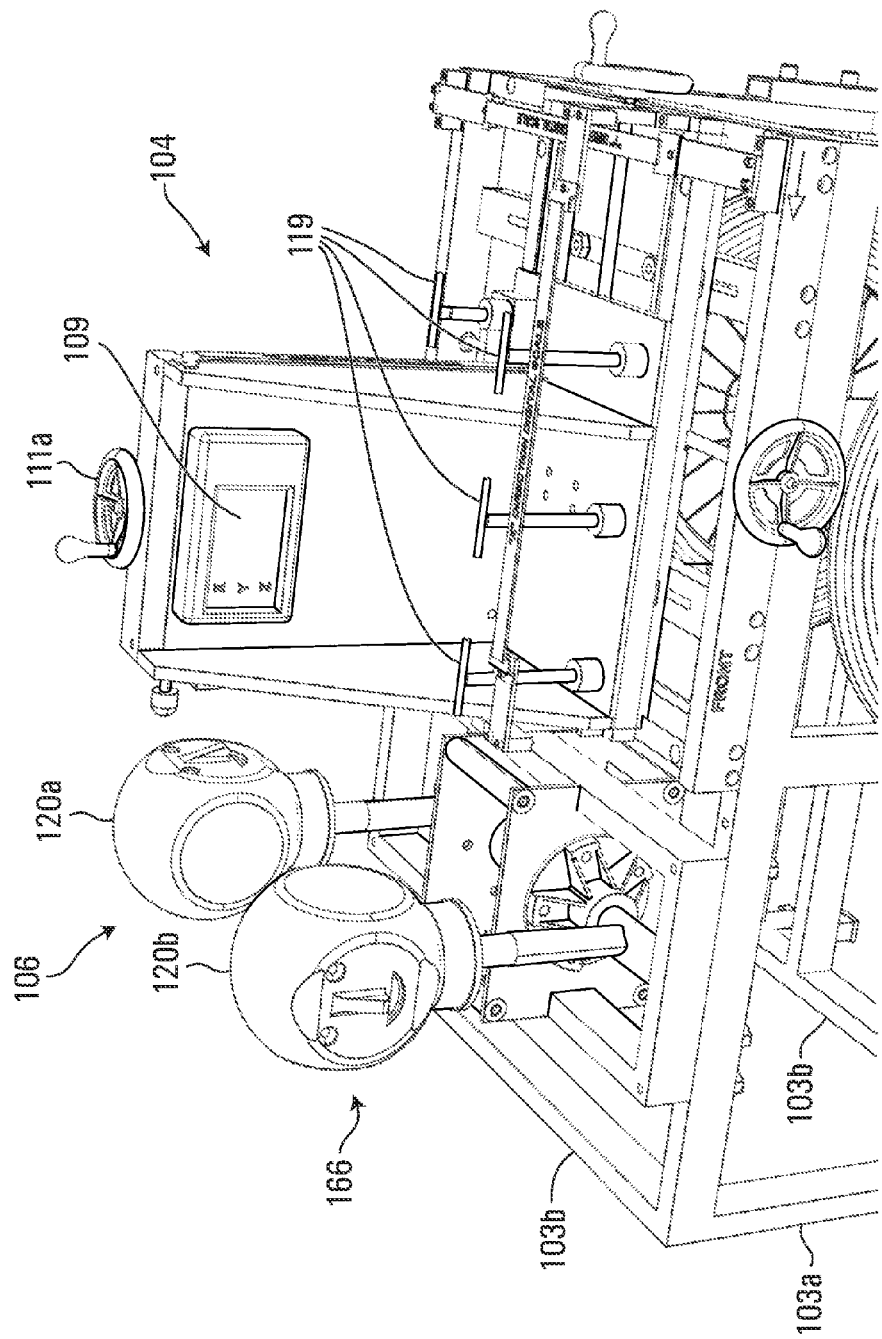
FIG. 11 is an enlarged partial rear top perspective view of the apparatus of FIG. 1 in the second configuration.
Figure 12:
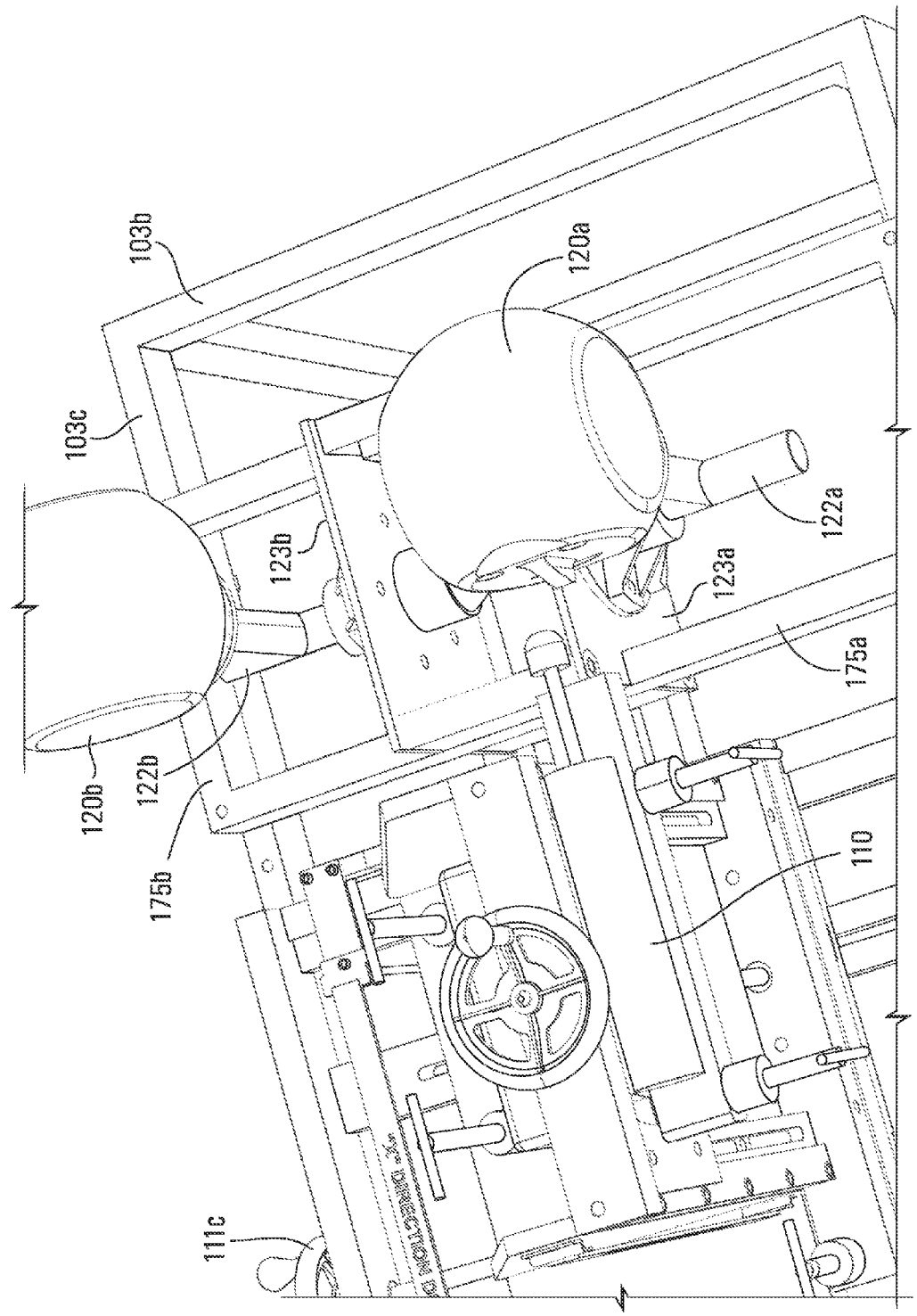
FIG. 12 is an enlarged partial front top perspective view of the apparatus of FIG. 1 in the second configuration.
Figure 13:
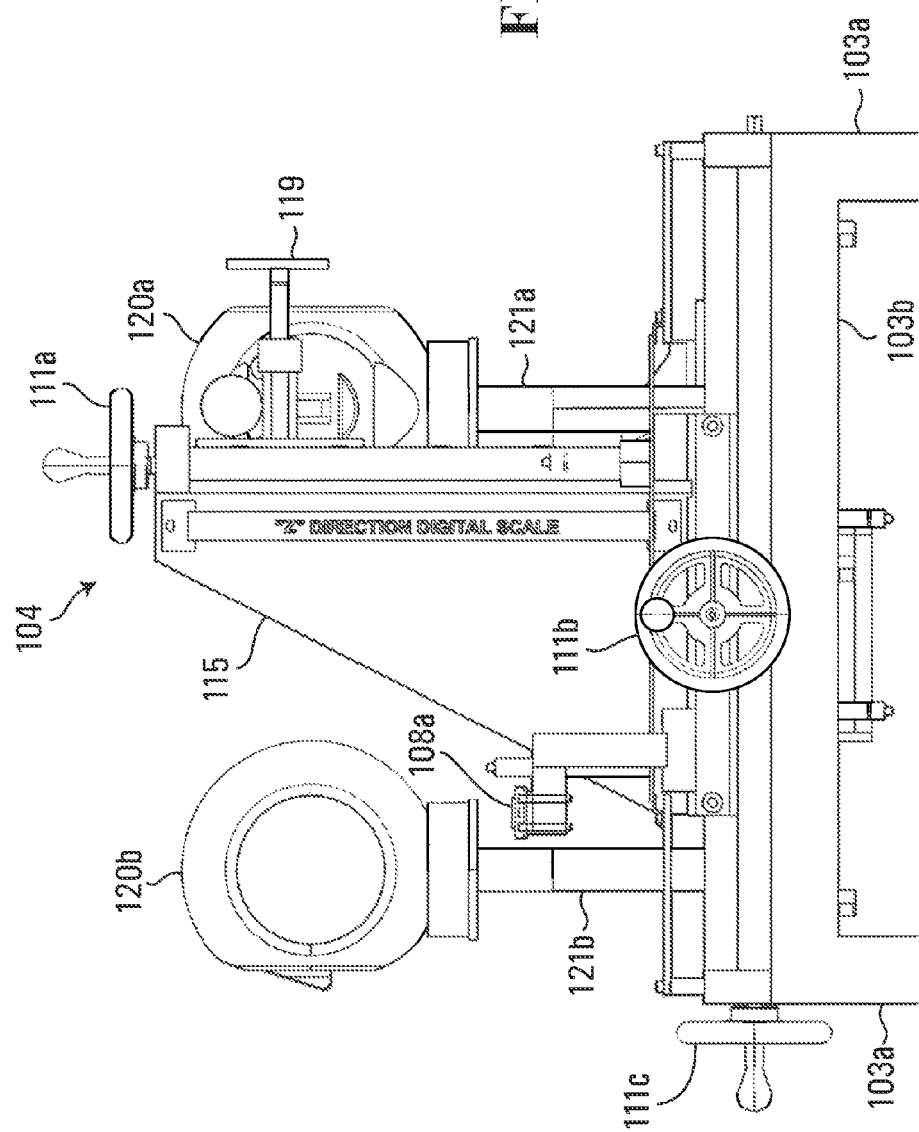
FIG. 13 is an enlarged partial side perspective view of the apparatus of FIG. 1 in the second configuration.
Figure 14:
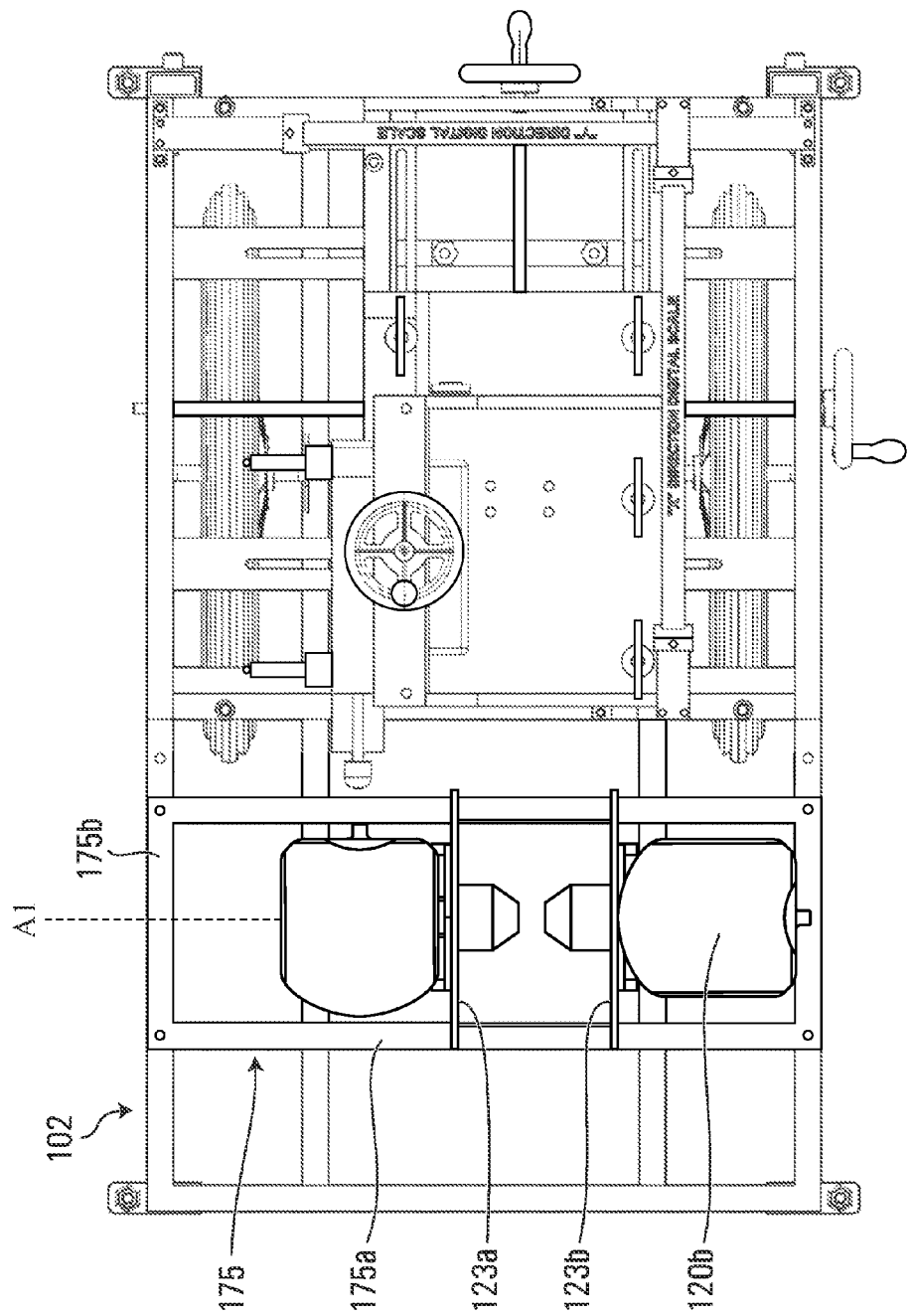
FIG. 14 is a top view of the apparatus of FIG. 1 in the second configuration.

As best shown in FIGS. 6 and 7, piston assembly unit 104 also includes an x-direction digital scale 108a, a y-direction digital scale 108b, and a z-direction digital scale 108c (collectively, digital scales 108) configured to provide x, y and z position measurements, respectively, to a display 109 (FIG. 5). Display 109 is a standard display such as a liquid crystal display (LCD) model Positron 3A by Lathemaster or the like. Display 109 is configured to display the x, y and z coordinates received from digital scales 108 through a connection provided for example by hardwire, between each digital scale 108 and display 109. The angle of piston 110 can also be measured for example manually using a protractor. The x, y and z coordinates and the angle can be appropriately recorded such as by entering them manually into device 140.

The components of frame 102, piston assembly unit 104, and head form assemblies 106,107 may be made of any suitable material having the requisite strength and durability characteristics to function in test apparatus 100, and are preferably formed of metal such as steel, aluminium, or the like.

In the first configuration shown in FIGS. 1-9, head form assembly 106 is mounted to frame 102 and is oriented so that head form 120b is aligned with piston device 110, where activation of piston 110 results in an impact of the piston against head form 120b.

In the second configuration shown in FIGS. 10-14, head form assembly 106 is mounted to frame 102 and is oriented so that head form 120a is aligned with piston 110, where activation of piston 110 results in an impact of the piston against head form 120a.

In the third configuration shown in FIGS. 15-19, head form assembly 107 is mounted to frame 102 and is oriented so that head form 120c is aligned with piston 110, where activation of piston 110 results in an impact of the piston against head form 120c.

Accordingly, the first configuration of apparatus 100 may be used for impact tests with simulated rotational neck movement limited to movement along or in alignment with a coronal plane, the second configuration of apparatus 100 may be used for impact tests with simulated rotational neck movement limited to movement along or in alignment with a sagittal plane, and the third configuration of apparatus 100 may be used for impact tests with simulated rotational neck movement limited to movement along or in alignment in an axial plane. Further, the position of the point of impact on the head form and the angle of impact may be adjusted with precision using positioning apparatus 199 to appropriately position piston 110. The actual position in 3-D space of the piston 110 can be displayed on display 109 for each impact. In this way testing can be standardized between helmets and multiple impact positions can be accurately calibrated for each helmet to provide a complete characterization of the helmet's force attenuation properties.

The energy produced by the piston 110 will depend in part upon the weight of the piston being driven by the cylinder, the amount of air pressure used to propel the piston, and the length along the piston stroke at which the impact occurs. By keeping these variables constant the impact force exerted upon each helmet can be maintained substantially consistent. For example, with a piston having a weight of about 1.3 kg, air pressure at 125 psi and impact occurring at 4.75 inches along the piston stroke length, with the angle of the piston set such that the piston travels perpendicularly to the impact surface of the head form, the piston may produce a suitable force against head forms 120. These values, and the subsequent accelerations produced in head forms 120, are expected to be consistent with concussion level forces in prior experimental situations, such as those disclosed in Zhang, Yang, King, "A Proposed Injury Threshold for Mild Traumatic Brain Injury", Journal of Biomechanical Engineering, April 2004 (hereinafter "Zhang et al."); Halstead P D, Alexander C F, Cook E M, Drew R C, "Hockey headgear and the adequacy of current designs and standards", Ashare A B, Safety in Ice Hockey, American Society for Testing and Materials, Philadelphia: 1998:93-101; and in McIntosh A, McCrory P, Comerford J, "The dynamics of concussive head impacts in rugby and Australian rules football", Med Sci Sports Exerc 2000, 32(12): 1980-1984, the contents of which are incorporated by reference herein. An exemplary set of test data that may be generated by apparatus 100 from impact tests configured according to these values is depicted in FIGS. 2526A-C, 28A-C and 29A-C, as described in more detail below.

Figure 21A:
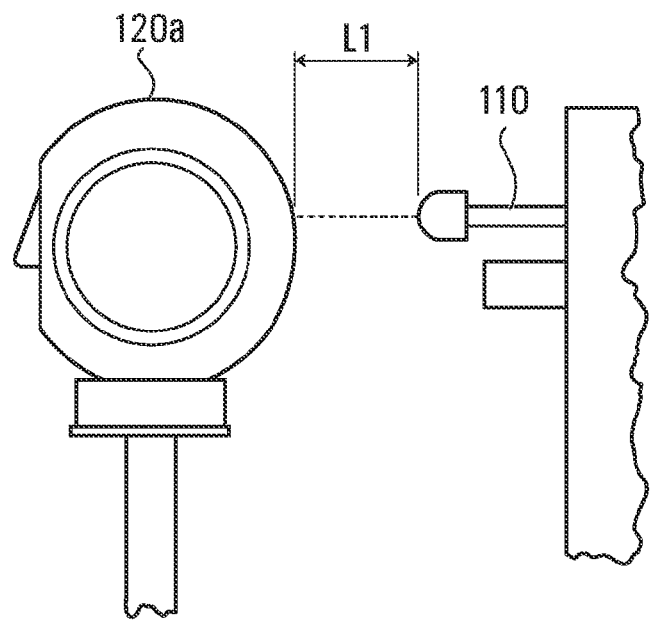
FIG. 21A is a partial cutaway view of a head form and an impact delivery unit of the apparatus of FIG. 1.
Figure 21B:
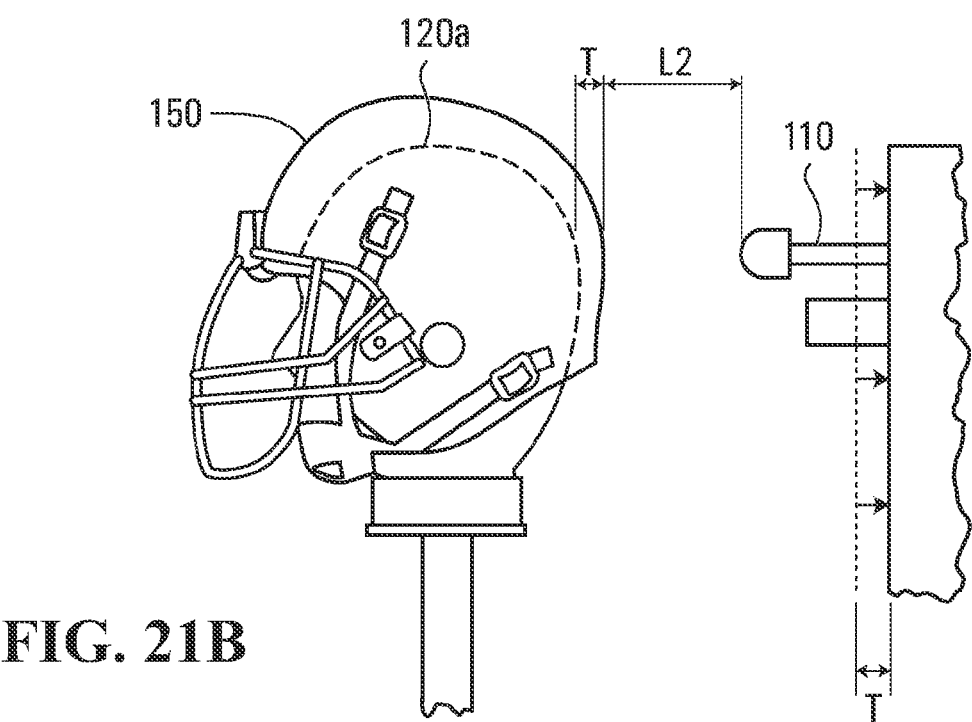
FIG. 21B is a partial cutaway view of a helmeted head form and an impact delivery unit of the apparatus of FIG. 1.

In order to maintain the length along the piston stroke at which impact occurs consistent between impacts against an unhelmeted head form versus impacts against a helmeted head form, the position of piston 110 can be adjusted to account for the thickness of the helmet. For example, as shown in FIGS. 21A and 21B, impacts against unhelmeted head form 120a may occur at a length L1 along the piston stroke, and impacts against helmeted head form 120a may occur at length L2 along the piston stroke. As shown, with helmet 150 having a thickness T, the longitudinal position of piston 110 can be adjusted away from head form 120a by a distance T in order to ensure L2 is equal to L1. The longitudinal position of piston 110 can be similarly adjusted to account for variances in thicknesses of different helmets. It should be noted that, while adjustment of the longitudinal position of piston 110 allows the length along the piston stroke at which impact occurs to be maintained consistent, there may be variations in the angle of impact to the helmet surface, due to variances in sizes and shapes of different helmets. While it will be appreciated that some of these variations can be accounted for by adjusting the angle and position in 3-D space of piston 110, in the presently disclosed embodiment these variations are not accounted for as the shape of the helmet is considered to contribute to the overall effect of the helmet in potentially reducing rotational accelerations when an impact force is directed to one or more particular locations on the head form.

Figure 22:
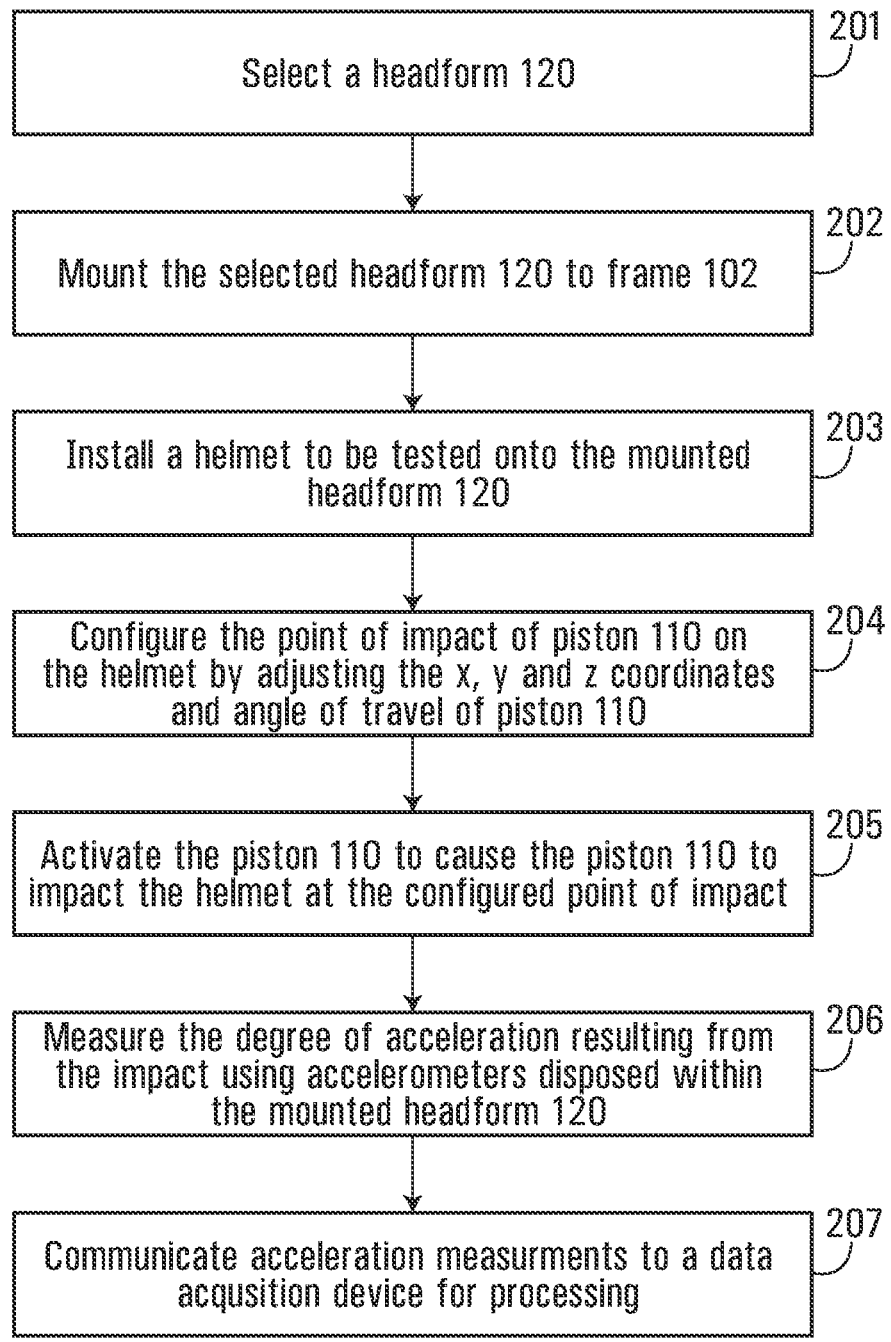
FIG. 22 is a flow diagram illustrating steps in a method exemplary of an embodiment of the present invention.

Broadly, a helmet impact test using apparatus 100 may be performed according to the steps shown in FIG. 22. Specifically, at one time, one of the three head forms 120 may be selected (step 201) for the test and mounted to frame 102 (step 202). A helmet 150 (FIG. 23) to be tested may then be installed onto the mounted head form 120 (step 203). A designated impact location 152 on helmet 150 may then be configured by adjusting the x, y and z coordinates and the angle of travel of piston 110 (step 204). The air pressure for the piston may be generated by a canister compressor, with the air pressure entering the pneumatic system being displayed on an analog gauge. Once the piston is in the desired position and the system is at the desired air pressure, the piston 110 may then be activated such as for example by a manual switch to thereby cause the piston 110 to accelerate toward the helmet and impact the helmet at the designated impact location (step 205), causing helmeted head form 120 to swing about shaft 122 and thereby generate a degree of acceleration in the mounted head form 120. An accelerometer 142 disposed within the mounted head form 120 measure the level of acceleration resulting from the impact (step 206) and communicate those measurements to data acquisition device 140 and then to a PC for processing (step 207). Steps 201 to 207 may be repeated multiple times for each of the three head forms 120 and for each of a number of desired impact points, as described in more detail below.

Rotational acceleration of a head form 120 during impact may be ascertained from measurements obtained by a corresponding accelerometer 142. It will be appreciated that the accelerometer may be able to deliver acceleration readings over a period of time during the rotation of the head form and will during that time period deliver a series of measurements of acceleration, which will include a maximum acceleration.

As noted above, in some embodiments accelerometers 142 may be uniaxial digital accelerometers. Specifically, the maximum linear acceleration of a head form 120 may be measured by placing a uni-axial accelerometer 142 at a point on the head form 120 furthest away from the axis of rotation, i.e. a point furthest away from the axis of shaft 122a, 122b or 122c, as the case may be. For example, as shown in FIGS. 20A, 20B, and 20C, each accelerometer 142 is positioned to correspond to a point of maximum tangential linear acceleration of its corresponding head form 120. Thus, for axial rotation accelerometer 142c is positioned in the forehead region of head form 120c, whereas for sagittal and coronal rotations, accelerometers 142a and 142b are positioned in the crown region of head forms 120a and 120b, respectively. It will be appreciated however that accelerometers 142 may be placed in any other suitable position within head forms 120. In some embodiments, accelerometers may be placed on an outer surface of the head form.

Figure 24B:
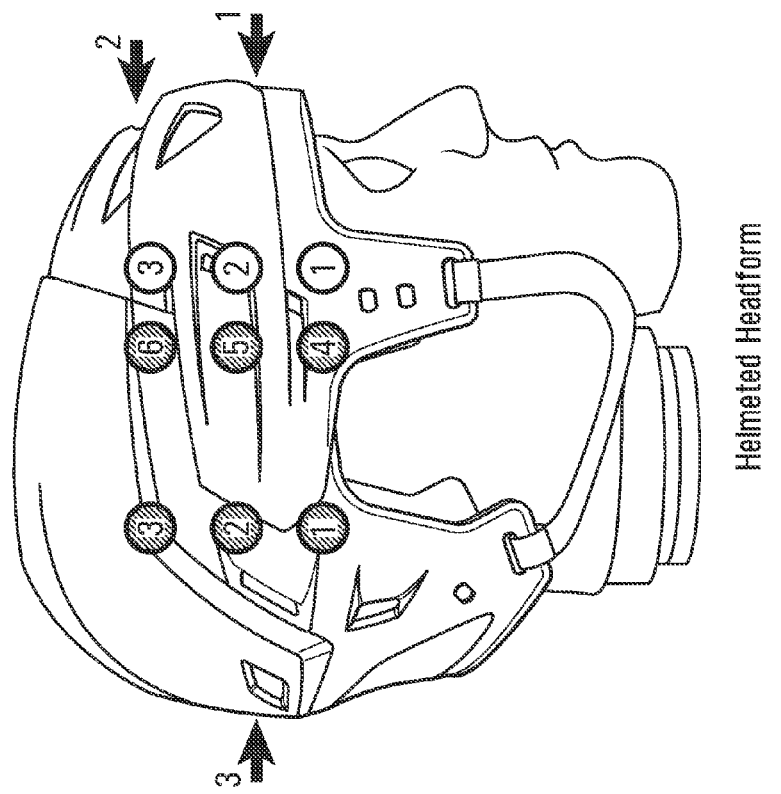
FIG. 24B is a diagram illustrating impact locations on a helmeted head form of the apparatus of FIG. 1.

The orientation of the accelerometers can be selected such that they measure an acceleration that is tangential to the curve defined by the radius from the axis of rotation. The linear accelerations can be directly converted to rotational acceleration (e.g. at data acquisition device 140) by dividing the linear acceleration by the radius from the centre of rotation to the location of measurement of the linear acceleration (e.g. a location on the accelerometer):

$$\alpha = \frac{a_T}{r}$$

where:
$\alpha$=angular acceleration
$a_T$=tangential acceleration
r=radius of curvature As will now be appreciated, multiple points of impact may be tested for any given helmet. For example, the points of impact may be chosen according to research published in Pellman E. J., Viano D. C., Tucker A. M., Casson I. R., "Concussion in professional football: location and direction of helmet impacts—Part 2", Neurosurgery 2003; 53:1328-1341, the contents of which are incorporated by reference herein. Pellman et al. analysed video footage of severe impacts during National Football League (NFL) games between 1996 and 2002, and catalogued 182 impacts based on the location of initial contact on the players' helmets. Although Pellman et al. only looked at head impacts in the context of football helmets, the Pellman et al. impact location classification scheme may be used for all helmet types to be tested. For example, impact locations depicted in FIGS. 24A and 24B may be used for standardized testing. Specifically, and as described in more detail below, impact locations illustrated by arrows 1, 2 and 3 may be used for impact tests relating to accelerations occurring in or along a sagittal plane, impact locations illustrated by cross-hatched circles 1, 2, 3, 4, 5 and 6 may be used for impact tests relating to accelerations occurring in or along a coronal plane, and impact locations illustrated by clear circles 1, 2 and 3 may be used for impact tests relating to accelerations occurring in or along an axial plane. Advantageously, use of a universally applicable classification system such as the one established by Pellman et al. allows test results to be reported in a standardized fashion.

In order to be concordant with established scientific literature, apparatus 100 is preferably adapted to meet concussive level rotational accelerations as reported by Zhang et al. An angular acceleration of $4.6 \times 10^3$ rad/s$^2$ was found by Zhang et al. to be sufficient to produce 25% chance of a concussion. When testing sports helmets in particular, impact forces simulated should not be so high as to be clinically irrelevant for the usual type of impact/injury experienced during amateur level play. It will be appreciated that impact velocities produced by apparatus 100 may be adjusted by varying the piston acceleration and/or velocity and/or the weight/mass of piston 110.

Prior to testing one or more helmets, apparatus 100 may be calibrated in each of the three axes (in each of the three orthogonal planes) and in different impact locations by consecutively impacting each unhelmeted head form 120 at each impact location with varying piston air pressures and with different piston impact weights until peak angular accelerations of 4000 rad/s$^2$ are achieved. The resulting pressures and weights for each plane that produces peak angular accelerations of 4000 rad/s$^2$ may subsequently be used during testing of one or more helmets.

Figure 24A:
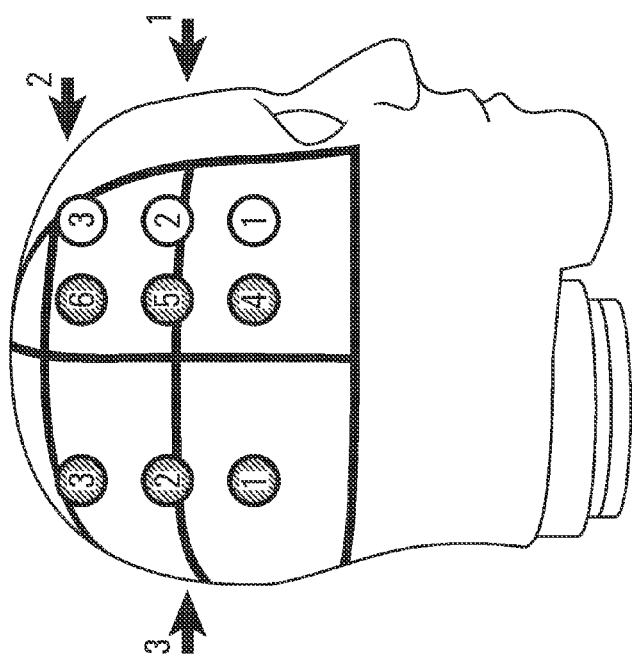
FIG. 24A is a diagram illustrating impact locations on a head form of the apparatus of FIG. 1.
Figure 25:
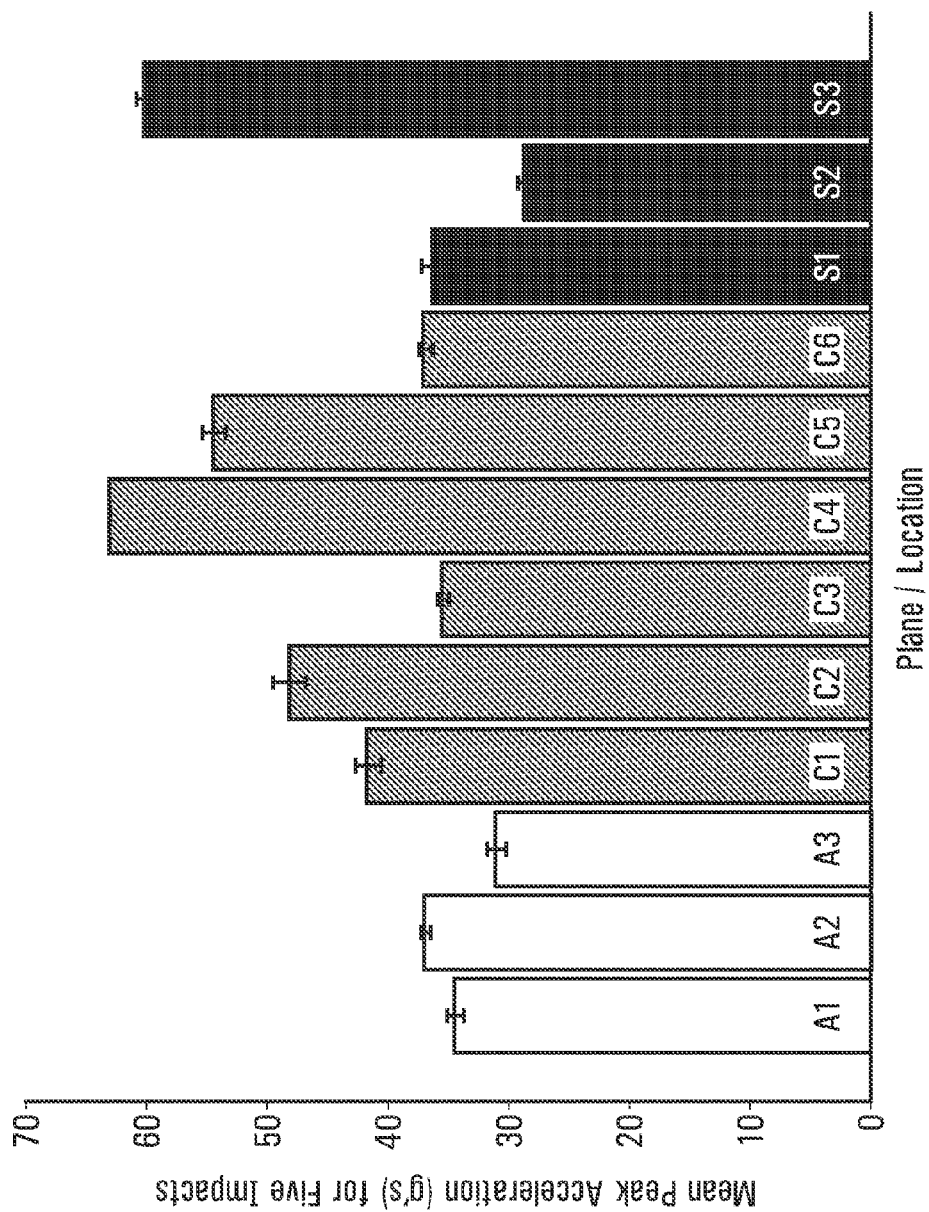
FIG. 25 is a graph illustrating exemplary mean peak accelerations measured by the apparatus of FIG. 1.
Figure 26A:
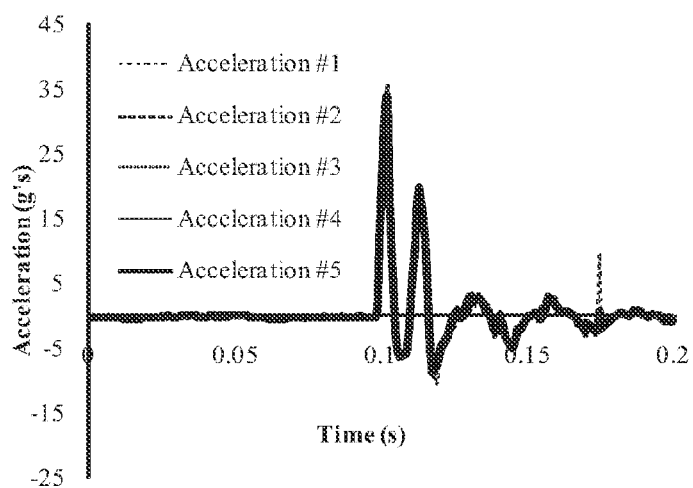
FIG. 26A is a graph illustrating exemplary acceleration tracings for axial impacts measured by the apparatus of FIG. 1.
Figure 26B:
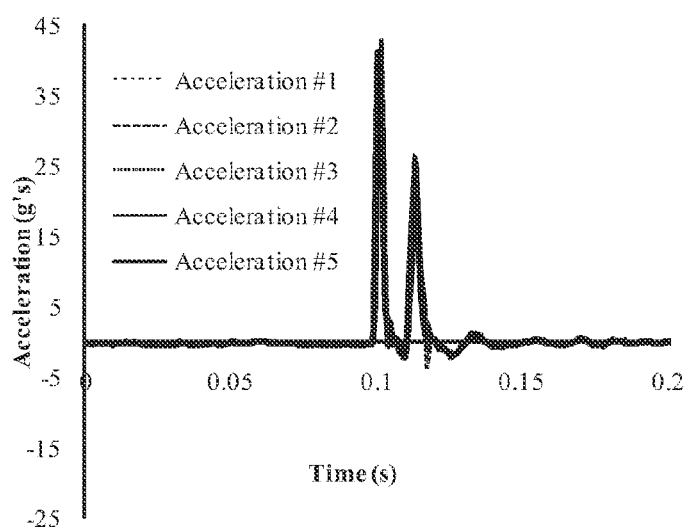
FIG. 26B is a graph illustrating exemplary acceleration tracings for coronal impacts measured by the apparatus of FIG. 1.
Figure 26C:
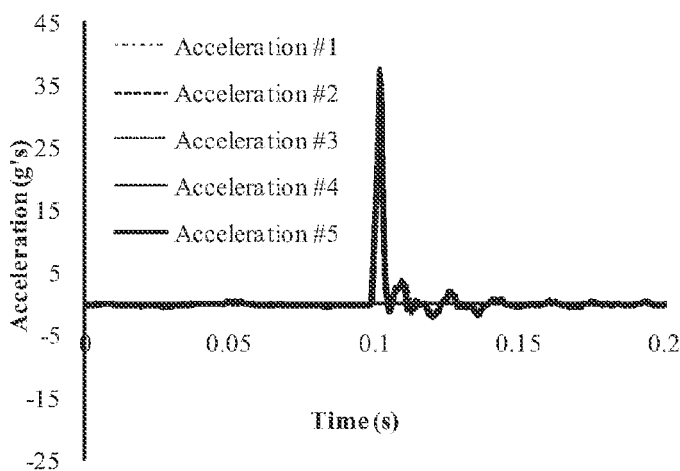
FIG. 26C is a graph illustrating exemplary acceleration tracings for sagittal impacts measured by the apparatus of FIG. 1.

Five consecutive impacts, for example, may be used in order to reach a level of accuracy wherein variability in peak acceleration falls within +/−2 g's. This level of accuracy was chosen as an arbitrary measure, and the accuracy may be increased by increasing the number of consecutive impacts performed. However, five impacts can provide an acceptable level of accuracy and allow efficient testing of helmets. Exemplary mean peak accelerations for five consecutive impacts at each impact location of FIG. 24A are illustrated by the bar graph shown in FIG. 25. Specifically, bars A1, A2 and A3 represent mean peak accelerations in an axial plane for five consecutive impacts at each of the impact locations on the head forms illustrated in FIG. 24A by clear circles 1, 2 and 3, respectively; bars C1, C2, C3, C4, C5 and C6 represent mean peak accelerations in a coronal plane for five consecutive impacts at each of the impact locations illustrated in FIG. 24A by cross-hatched circles 1, 2, 3, 4, 5 and 6, respectively; and bars S1, S2 and S3 represent mean peak accelerations in a sagittal plane for five consecutive impacts at each of the impact locations illustrated in FIG. 24A by arrows 1, 2 and 3, respectively. The repeatability of the acceleration response of head form 120 to five separate impacts is illustrated by the exemplary axial, coronal, and sagittal tracings shown in FIGS. 26A, 26B and 26C, respectively.

Figure 27:
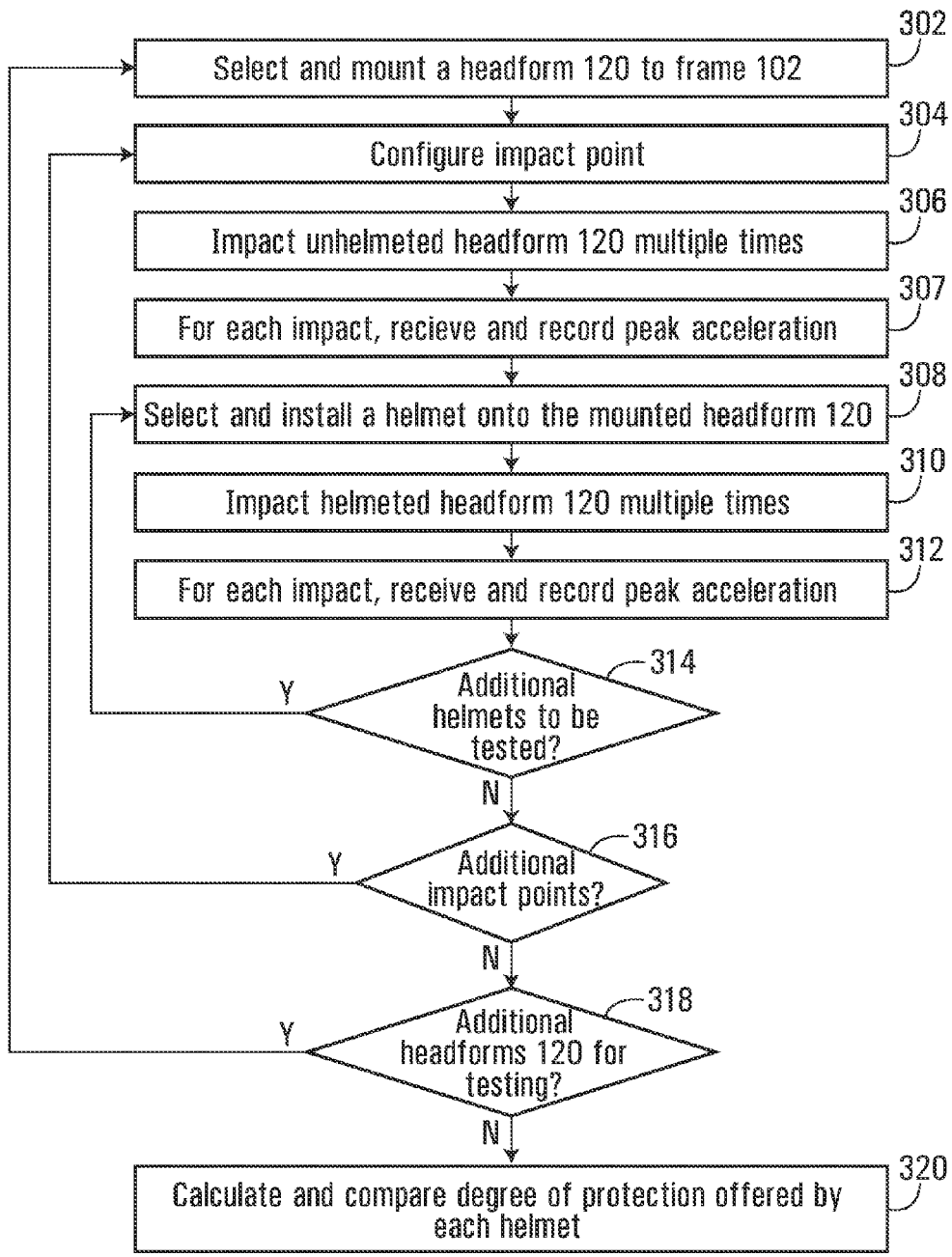
FIG. 27 is a flow diagram illustrating steps in a method exemplary of an embodiment of the present invention.

Test apparatus 100 may be used to measure and compare the degree of protection against rotational acceleration afforded by different helmets according to the steps shown in FIG. 27. As shown, initially one of the three head forms 120 is selected for testing and is mounted to frame 102 (step 302). Next, a designated impact location, or impact point, is configured (step 304) and a baseline acceleration profile for the designated location on the unhelmeted head form 120 is recorded (steps 306 to 307). Specifically, the unhelmeted head form 120 is impacted multiple times (e.g. five times) at the configured designated location (step 306), with other impact variables (e.g. air pressure, piston stroke length, and piston head weight) being kept constant. For each impact, a peak acceleration produced by the impact as measured by an accelerometer 142 of mounted head form 120 is received and recorded by data acquisition device 140 (step 307). The degree of variance in the impact measurements indicates the precision of apparatus 100 for that impact point, and may in some embodiments fall in the range of +/−2 g's. Next, one of a group of helmets being compared is selected and installed onto the mounted head form 120 (step 308), and an acceleration profile for the helmet is recorded (steps 310 to 312). Specifically, the helmeted head form 120 is impacted multiple times (e.g. five times) at the configured designated location (step 310), with other impact variables (e.g. air pressure, piston stroke length, and piston head weight) being kept constant. For each impact, a peak acceleration produced by the impact as measured by an accelerometer 142 of mounted head form 120 is received and recorded by data acquisition device 140 (step 312).

Steps 308 to 312 are repeated for each helmet in the group of helmets being compared (step 314) so that an acceleration profile for each helmet in the group of helmets being compared is recorded.

Steps 304 to 314 are repeated for each impact location of a predetermined set of impact locations (step 316) so that, for each helmet being compared, an acceleration profile for each location is recorded. As will now be appreciated, the impact locations illustrated in FIG. 23A may be used as the predetermined set of impact locations.

Steps 302 to 316 are repeated for each head form 120 (step 318) so that, for each helmet being compared, acceleration profiles for each axis of rotation are recorded.

Once acceleration profiles for each helmet have been determined, a degree of protection against rotational acceleration afforded by each helmet may be calculated and compared for each impact location (step 320). Specifically, for any given impact location, any change in acceleration between the unhelmeted (baseline) acceleration profile and the acceleration profile for the helmeted head form may be attributed to protection afforded by the helmet itself. Thus, protection afforded by the helmet at each impact location is characterized. More specifically, mean peak acceleration measurements for each impact location taken from both the baseline profile and the helmet profile may be compared. Similarly, mean peak acceleration ratios for a given impact location between any two helmets may be compared using the same approach. By repeating the calculations, it is possible to contrast helmet protection afforded by all of the helmets tested.

As noted, this process can be repeated for each of the three head forms 120a, 120b, 120c to provide mean peak acceleration measurements for each of the three axes (and corresponding sagittal, coronal and axial planes).

It should also be noted that mean peak rotational accelerations between different helmets could be compared directly with each other instead of comparing percentage reductions relative to a baseline.

To determine whether certain classes of helmets provide better rotational acceleration protection, the tested helmets may be divided into categories, and Spearman rank correlations may then be used to determine if some categories offer better rotational protection. For example, to determine whether higher priced helmets provide better rotational acceleration protection, the tested helmets may be divided into four categories according to price: low, medium, high, and elite. One can then compare rotational acceleration protection afforded by a particular helmet, as evidenced by the reduction of mean peak acceleration from the unhelmeted baseline, and analyse whether higher priced helmets have a tendency towards better impact protection.

Once measurements have been gathered, a one-way analysis of variance (ANOVA) may be conducted to compare the overall effect of each test helmet at reducing rotational acceleration compared to the unhelmeted head form. This can be done by comparing the mean peak acceleration at a particular impact location for a particular helmet to the unhelmeted mean peak acceleration at the same impact location with the same impact parameters. Since all impact variables are kept constant, the effect of any reduction in mean peak acceleration is due to the protective qualities of the helmet.

Figure 28A:
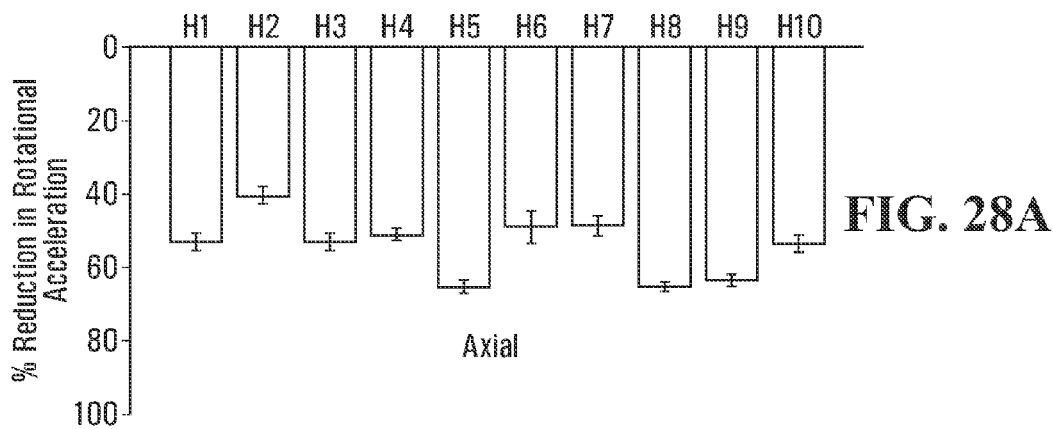
FIG. 28A is a graph illustrating exemplary percent reductions in axial rotational acceleration for each of ten test helmets as measured by the apparatus of FIG. 1.
Figure 28B:
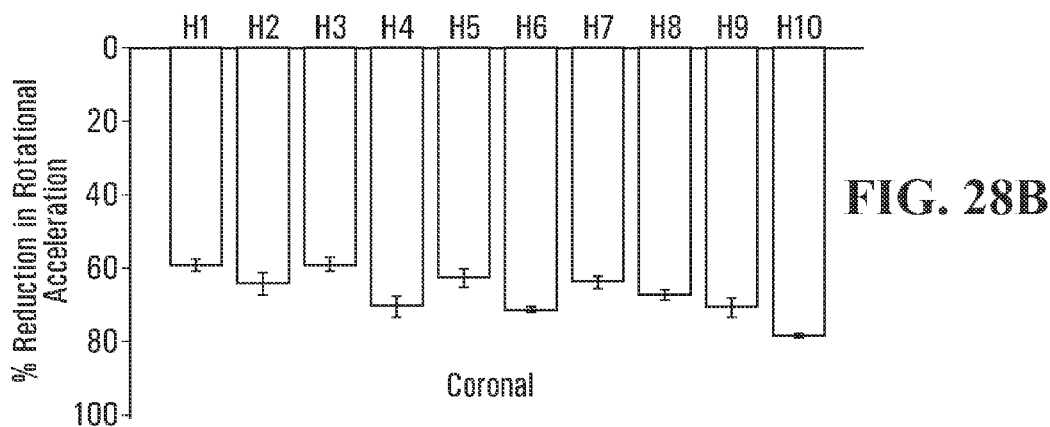
FIG. 28B is a graph illustrating exemplary percent reductions in coronal rotational acceleration for each of ten test helmets as measured by the apparatus of FIG. 1.
Figure 28C:
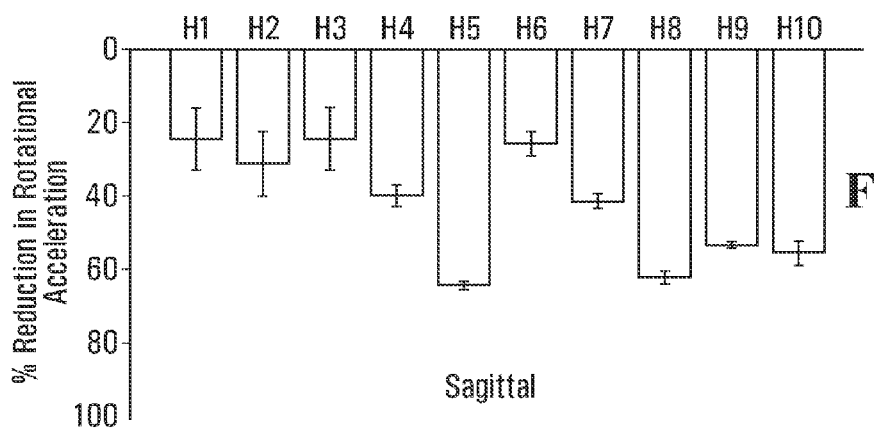
FIG. 28C is a graph illustrating exemplary percent reductions in sagittal rotational acceleration for each of ten test helmets as measured by the apparatus of FIG. 1.

A post hoc comparison using Dunnett's HSD test may be used to analyse whether each test helmet provides a statistically significant reduction in rotational acceleration at each location when compared to the unhelmeted head form. An exemplary set of data that may result from tests conducted on an exemplary set of test helmets H1 through H10 is shown in FIGS. 28A, 28B, and 28C. Specifically, the data can be presented in graph form as the percent reduction in rotational acceleration for each test helmet. In this exemplary set of data, it is shown that all test helmets significantly reduced rotational acceleration compared to the unhelmeted head form.

Similarly, acceleration differences between test helmets in each of the planes and impact locations may be assessed. Specifically, a one-way ANOVA may be conducted to compare the percent reduction in rotational acceleration between each test helmet at each impact location and plane. A post hoc comparison using Tukey's HSD test may be used to analyze whether there are statistically significant differences in rotational acceleration between test helmets at each impact location within a given plane. In this way the protective qualities of a helmet can be dissected to specific impact locations to allow specific design and construction improvements and enhance helmet safety.

Figure 29A:
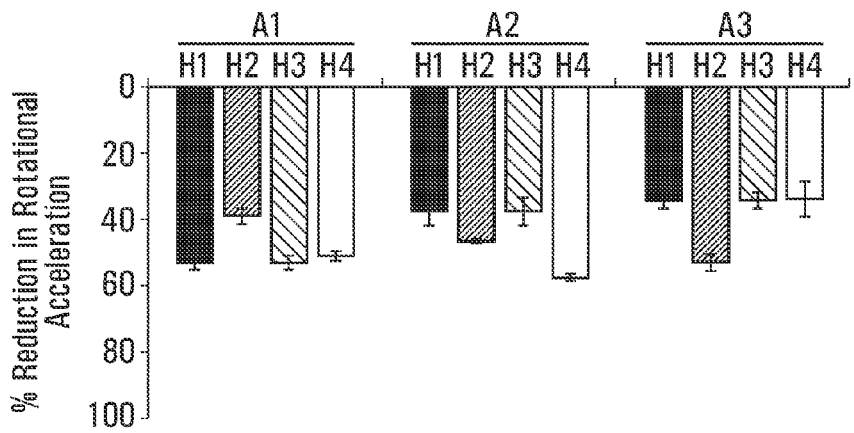
FIG. 29A is a graph illustrating exemplary percent reductions in axial rotational acceleration at each of three impact locations for each of four test helmets as measured by the apparatus of FIG. 1.
Figure 29B:
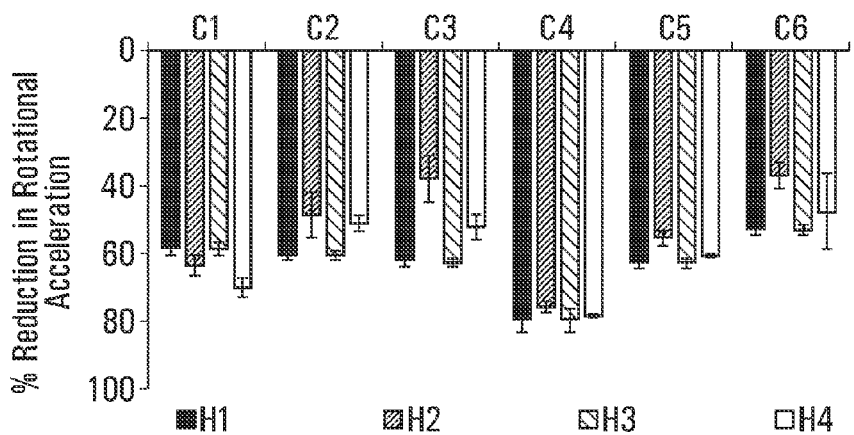
FIG. 29B is a graph illustrating exemplary percent reductions in coronal rotational acceleration at each of six impact locations for each of four test helmets as measured by the apparatus of FIG. 1.
Figure 29C:
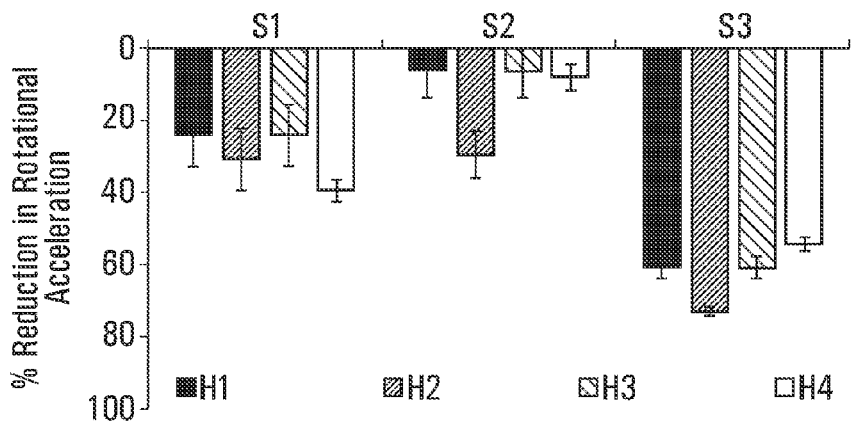
FIG. 29C is a graph illustrating exemplary percent reductions in sagittal rotational acceleration at each of three impact locations for each of four test helmets as measured by the apparatus of FIG. 1.

An exemplary set of data that may result from tests conducted on an exemplary set of test helmets H1 through H4 is shown in FIGS. 29A, 29B, and 29C. Specifically, the data is presented in graph form as the percent reduction in rotational acceleration for each test helmet at specific impact locations and planes, where each graph represents one of the three planes and the impact locations A1, A2, A3, C1, C2, etc represent the impact locations shown in FIGS. 24A and 24B.

In addition, acceleration differences within a particular test helmet at each plane may also be assessed. Specifically, a one-way ANOVAs may be conducted to compare the percent reduction in rotational acceleration provided by a particular test helmet at each impact location in each plane.

In general, helmets consist of a shell, foam padding, and a chin strap. It is widely believed that the shell disperses the impact force over a larger surface area and the foam padding reduces acceleration forces. The ideal shell should be: 1) light, 2) crack resistant, 3) allow proper ventilation, 4) disperse the impact force over a larger surface area, and 5) have a low level of friction to reduce rotational forces. It is known that helmet foam reduces linear acceleration forces. Therefore, a thicker and denser foam within the shell, provides greater protection. Thus, a preferred helmet should contain a light, smooth, round shell and very thick foam. Practicalities intervene as foam thickness is limited by weight and volume in the design of a wearable sport helmet. Various manufacturers produce helmets of varying shells, contours, and ventilation spaces. They also have different foam types and arrangements within the shell.

It will be also appreciated that when a given force is exerted on the impacted head form with a helmet attached, the acceleration of the actual head form with the helmet mounted thereon, will also be dependent upon several factors including the total mass of the head form and helmet as well as the amount of cushioning effect of the force that occurs in the interaction between the piston, outer helmet shell, inner foam cushioning and head form. The precise impact and absorption interactions that occur with the helmet and head form are difficult to precisely analyse. However it will be expected that all other factors being equal, the heavier a helmet is, the lower will be the resultant acceleration of the helmet and head form combination (when the helmet is secured to the head form). When testing as between several different helmets, the mass of each head form will remain constant between different helmets during testing but the mass of the different helmets may vary. Therefore, a heavier helmet can be expected to have a lower acceleration than a lighter helmet. The foregoing test apparatus and methods only measure the actual accelerations experienced by the head form when cushioned by the helmet. The apparatus and methods do not distinguish between or identify the actual basis or mechanism why the head forms may have experienced different accelerations when protected by each of the helmets. Advantageously, the apparatus and methods disclosed herein allow helmet testing and evaluation to be accomplished by breaking down each event into specific isolated movements, and thus producing quantifiable, accurate, reliable and reproducible measurements of rotational acceleration at injury-relevant impact locations and planes with various degrees of impact force. Such measurements allow comparison of differences in rotational force protection at specific locations in commercially available helmets, and enables modifications to be made and retested to produce more focused and measurable improvements. Knowing the importance of rotational acceleration in concussion causation and the fundamental lack of reliable and reproducible test procedures that simulate rotational impacts to helmets, the methods and apparatus described above bridge the fundamental gap that exists between the science of concussion biomechanics and the engineering of helmet testing.

While apparatus 100 has been described as including three head forms 120, it will be appreciated that in other embodiments fewer head forms may be used. For example, a single head form 120 may be used in conjunction with a suitable mechanism for selectively limiting rotational movement of the single head form 120 to three separate axes each perpendicular to one of a sagittal, a coronal and an axial plane, respectively.

Other modifications will be apparent to those skilled in the art and, therefore, the invention is defined in the claims.

Although not specifically described in detail herein, suitable modifications may be made to the embodiments described by persons skilled in the art depending on a particular application. Of course, the foregoing embodiments are intended to be illustrative only and in no way limiting. The described embodiments of carrying out the invention are susceptible to many modifications of form, arrangement of parts, details and order of operation. The invention, rather, is intended to encompass all such modification within its scope, as defined by the claims.

When introducing elements of the present invention or the embodiments thereof, the articles "a," "an," "the," and "said" are intended to mean that there are one or more of the elements. The terms "comprising," "including," and "having" are intended to be inclusive and mean that there may be additional elements other than the listed element.

What is claimed is:

1. An apparatus comprising:
   a frame;
   an impact delivery unit for delivering an impact force;
   at least one head form adapted to be mounted to said frame such that said impact delivery unit can deliver an impact force to a designated location on said at least one head form;
   said head form being configured to have a helmet installed thereon;
   said at least one head form being operable to be:
      (i) selectively rotated about a first axis of rotation of a plurality of axes of rotation such that when selected to be rotated about said first axis of rotation, the rotation of said at least one head form is constrained so that said at least one head form is only capable of rotation about said first axis of rotation of said plurality of axes;
      (ii) selectively rotated about a second axis of rotation of said plurality of axes of rotation such that when selected to be rotated about said second axis of rotation, the rotation of said at least one head form is constrained so that said at least one head form is only capable of rotation about said second axis of rotation;
   a measuring system for providing an indicator of the rotational acceleration of said at least one head form when rotated about each of said plurality of axes;
   wherein said system is operable, when said impact delivery unit delivers a plurality of impact forces to said designated location on said at least one head form, such that said at least one head form can be selectively constrained to rotate separately about each axis of rotation of said plurality of axes, said measurement system is operable to provide indicators of rotational accelerations about each of said plurality of axes of rotation of said at least one head form during separate rotations about each axis of said plurality of axes of rotation.

2. An apparatus as claimed in claim 1 wherein said at least one head form comprises a plurality of head forms and each of said plurality of head forms is rotatable only about a single respective axis of rotation of said plurality of axes of rotation, and wherein each of said plurality of head forms is adapted to be selectively mounted to said frame such that said impact delivery unit can respectively deliver an impact force to designated locations on each head form of said plurality of head forms and wherein when said impact delivery unit delivers an impact to said designated locations on said each head form, said each head form rotates about a selected single axis of rotation of said plurality of axes, and wherein said measurement system provides indicators of rotational acceleration about each of said plurality of axes of rotation during separate rotations of each of said plurality of head forms about each of said plurality of axes of rotation.

3. An apparatus as claimed in claim 2 wherein each of said plurality of head forms may be selectively configured on said frame for rotation about a different axis of rotation of said plurality of axes of rotation.

4. An apparatus as claimed in claim 2 wherein said impact force is a substantially constant impact force that can impact upon each of said plurality of head forms.

5. An apparatus as claimed in claim 2, wherein said measurement system comprises a measurement device associated with each of said plurality of head forms, each measurement device for measuring an acceleration of a different one of said plurality of head forms, wherein when said impact delivery unit delivers an impact to designated locations on each of said plurality of head forms, each said measurement device associated with each said head forms measures the acceleration of each said head form.

6. An apparatus as claimed in claim 5 wherein measurement system provides indicators of peak rotational accelerations about each of said plurality of axes of rotation.

7. An apparatus as claimed in claim 2 wherein measurement system provides indicators of peak rotational accelerations about each of said plurality of axes of rotation.

8. An apparatus as claimed in claim 7 wherein said plurality of head fauns comprise first, second and third head forms, and wherein said plurality of different axes of rotation comprise first, second and third axes of rotation, said first axis being perpendicular to a sagittal plane, said second axis being perpendicular to a coronal plane, and said third axis being perpendicular to an axial plane, and wherein said first head form is rotatable only about said first axis, said second head form is rotatable only about said second axis, and said third head form is rotatable only about said third axis.

9. An apparatus as claimed in claim 2 wherein said plurality of axes of rotation comprises a first axis of rotation and a second axis of rotation.

10. An apparatus as claimed in claim 9 wherein said plurality of axes of rotation further comprises a third axis of rotation.

11. An apparatus as claimed in claim 10 wherein said each of said first, second and third axes of rotation is associated with a respective one of a corresponding plurality of different planes of rotation, whereby said at least one head form is constrained to rotate in alignment with only one of said different planes of rotation at any time.

12. An apparatus as claimed in claim 11 wherein said plurality of planes of rotation comprise a sagittal plane through one of said plurality of head forms.

13. An apparatus as claimed in claim 12 wherein said plurality of planes of rotation further comprise a coronal plane through one of said plurality of head forms.

14. An apparatus as claimed in claim 2 wherein each of said plurality of head forms is adapted to receive a helmet.

15. An apparatus as claimed in claim 14, wherein said impact delivery unit for delivering an impact force comprises a piston assembly having a piston operable to respectively impact said helmet when said helmet is received on said each head form at said designated locations.

16. An apparatus as claimed in claim 2 wherein said measurement system comprises a separate measuring device for each of said plurality of head foams, each measuring device for measuring acceleration along a respective axis of rotation of said plurality of axes of rotation.

17. An apparatus as claimed in claim 16 wherein each said separate measuring device comprises an accelerometer for measuring an acceleration of said head form.

18. An apparatus as claimed in claim 1 wherein said at least one head form comprises a plurality of head forms each being adapted to be mounted to said frame such that said impact delivery unit can deliver an impact force to each said head form, and wherein each one of said plurality of head forms is adapted to be interchangeably mounted to said frame so as to be rotatable about a single respective axis of rotation of said plurality of different axes of rotation.

19. An apparatus as claimed in claim 1 wherein measurement system provides indicators of peak rotational accelerations about each of said plurality of axes of rotation.

20. An apparatus as claimed in claim 1 wherein said impact delivery unit comprises a piston device operable to impact a head form.

21. An apparatus as claimed in claim 20 wherein said impact delivery unit further comprises a piston assembly mounted to said frame, said piston assembly adapted to support said piston device.

22. An apparatus of claim 1, wherein said at least one head form is adapted to have a helmet mounted thereon.

23. An apparatus as claimed in claim 1, wherein said measurement system comprises a plurality of measuring devices each for measuring acceleration along a respective axis of rotation of said plurality of axes of rotation.

24. An apparatus as claimed in claim 23 further comprising a positioning and support apparatus for adjusting the position in 3-D space of said piston relative to said helmet received on said each head form to thereby be able to adjust each point of impact of said plurality of points of impacts.

25. An apparatus as claimed in claim 24, wherein said positioning and support apparatus is operable to adjust said position of said piston in height, longitude and latitude of said piston relative to said helmet received on said each head form.

26. An apparatus as claimed in claim 25, further comprising a z-direction scale, an x-direction scale, and a y-direction scale for measuring height, longitude and latitude coordinates of said piston; and a display adapted to display said height, longitude and latitude coordinates.

27. An apparatus as claimed in claim 1 further comprising a data device in communication with said measuring system for receiving and processing the indicator of the acceleration of said at least one head form when rotated about each of said plurality of axes to generate a rotational acceleration about each of said plurality of axes.

28. A method of testing a helmet, said method comprising:
providing an impact delivery unit having a force actuator for delivering an impact force;
providing at least one head form such that said impact delivery unit can deliver an impact force to said at least one head form;
impacting said at least one head form with said force actuator so as to rotate said at least one head form about a plurality of different axes of rotation in sequence;
selectively rotating said at least one head form about a first axis of rotation of said plurality of axes of rotation such that when selected to be rotated about said first axis of rotation, the rotation of said at least one head form is constrained so that said at least one head form is only capable of rotation about said first axis of rotation;
selectively rotating said head faun about a second axis of rotation of said plurality of axes of rotation such that when selected to be rotated about said second axis of rotation, the rotation of said at least one head form is constrained so that said at least one head form is only capable of rotation about said second axis of rotation;

obtaining an indicator of each acceleration of said at least one head form when rotated about each of said plurality of axes;

from the indicators of acceleration, determining the rotational acceleration of each said head form during rotations about each of said plurality of axes of rotation.

29. A method as claimed in claim 28 wherein said indicators are indicators of peak rotational accelerations.

30. A method for testing a helmet, said method comprising:

selecting a first head form from a plurality of head forms, each of said plurality of head forms each being configured to rotate only about a different axis of rotation of a plurality of axes of rotation;

installing a helmet on said first head form;

exerting a force against said helmet at a designated location to thereby cause said selected first head form to rotate about a first axis of rotation, wherein said first head form is constrained so that it is only capable of rotation about said first axis of rotation;

measuring an indicator of rotational acceleration about said first axis of rotation of said selected first head form;

determining a rotational acceleration of said selected first head form about said corresponding first axis of rotation;

selecting a second head form from a plurality of head forms;

installing said helmet on said second head form;

exerting a force against said helmet at a designated location to thereby cause said selected second head form to rotate about said second axis of rotation, wherein said second head form is constrained so that it is capable only of rotation about said second axis of rotation;

measuring an indicator of rotational acceleration about said second axis of said selected second head form;

determining a rotational acceleration of said selected second head form about said second axis of rotation.

31. A method as claimed in claim 30 wherein said indicators are indicators of peak rotational accelerations.

32. A method as claimed in claim 31 wherein each of said plurality of axes of rotation is associated with a different corresponding one of a plurality of planes of rotation.

33. A method as claimed in claim 30 further comprising:

selecting a third head form from a plurality of head forms;

installing said helmet on said third head form;

exerting a force against said helmet at a designated location to thereby cause said selected head form to rotate about said third axis of rotation, wherein third head form is constrained so that it is capable only of rotation about said third axis of rotation;

measuring an indicator of rotational acceleration about said third axis of said selected head form;

determining a rotational acceleration of said selected head form about said third axis of rotation.

34. A method as claimed in claim 33 wherein said indicators are indicators of peak rotational accelerations.

35. A method as claimed in claim 33 wherein said first, second and third axes of rotation are orthogonal to each other.

36. An apparatus comprising:

at least one head form;

a helmet configured for attachment to said at least one head form;

an impact delivery unit for delivering an impact force to said helmet at at least one designated location when said helmet is attached to said at least one head form;

said at least one head form being operable to be:

(i) selectively rotated about a first axis of rotation of a plurality of axes of rotation such that when selected to be rotated about said first axis of rotation, the rotation of said at least one head form is constrained so that said at least one head form is only capable of rotation about said first axis of rotation of said plurality of axes;

(ii) selectively rotated about a second axis of rotation of said plurality of axes of rotation such that when selected to be rotated about said second axis of rotation, the rotation of said at least one head form is constrained so that said at least one head form is only capable of rotation about said second axis of rotation;

a measuring system for providing an indicator of the acceleration of said at least one head form when rotated about each of said plurality of axes;

wherein when said impact delivery unit delivers an impact to said at least one head form, said measurement device associated with each said head from measures the acceleration of each said head form during rotations about each of said plurality of axes of rotation.

* * * * *